(12) United States Patent
Mistrello et al.

(10) Patent No.: US 9,957,306 B2
(45) Date of Patent: May 1, 2018

(54) HYPOALLERGENIC VARIANTS OF MAL D 1, THE MAJOR ALLERGEN FROM MALUS DOMESTICA

(75) Inventors: Giovanni Mistrello, Milan (IT); Stefania Zanotta, Milan (IT); Daniela Roncarolo, Milan (IT)

(73) Assignee: LOFARMA S.P.A., Milan (IT)

( * ) Notice: Subject to any disclaimer, the term of this patent is extended or adjusted under 35 U.S.C. 154(b) by 1065 days.

(21) Appl. No.: 14/234,795

(22) PCT Filed: Jul. 31, 2012

(86) PCT No.: PCT/EP2012/064944
§ 371 (c)(1),
(2), (4) Date: Apr. 14, 2014

(87) PCT Pub. No.: WO2013/017591
PCT Pub. Date: Feb. 7, 2013

(65) Prior Publication Data
US 2014/0294878 A1    Oct. 2, 2014

(30) Foreign Application Priority Data
Aug. 3, 2011 (IT) .......................... MI2011A001489

(51) Int. Cl.
C07K 14/415 (2006.01)
A61K 36/73 (2006.01)
A61K 39/36 (2006.01)
A61K 39/00 (2006.01)

(52) U.S. Cl.
CPC .......... *C07K 14/415* (2013.01); *A61K 39/36* (2013.01); *A61K 2039/55505* (2013.01); *A61K 2039/577* (2013.01); *A61K 2039/70* (2013.01)

(58) Field of Classification Search
None
See application file for complete search history.

(56) References Cited

FOREIGN PATENT DOCUMENTS

| EP | 2028188 | 2/2009 | |
|---|---|---|---|
| WO | WO 03/096869 | * 11/2003 | .......... C07K 14/415 |
| WO | 2004039834 | 5/2004 | |
| WO | 2007073907 | 7/2007 | |

OTHER PUBLICATIONS

Uehara et al (Allergology International, 2001, 50: 57-62).*
Cromwell (Allergy Frontiers: Future Perspectives edited by Pawankar et al., 2010, pp. 31-47).*
Son et al (Eur. J. Nutr., 1999, 38:201-215).*
Holm Jens, et al., Allergy Vaccine Engineering . . . , Journal of Immunology, American Assoc. of Immunologists, vol. 173, No. 8, 2004.
Holm J., et al., Molecular Basis of Allergic Cross-Reactivity Between Group 1 . . . , Journal of Chromatography B: Biomedical Applications, Elsevier Science Publishers, NL, vol. 756, No. 1-2, 2001.
Thalhamer T., et al., Designing Hypoallergenic Derivatives for Allergy . . . , Journal of Allergy and Clinical Immunology, Mosby, Inc., vol. 125, No. 4, 2010.
International Search Report issued in counterpart PCT Application No. PCT/EP/2012/064944 dated Nov. 2012.
Written Opinion of International Searching Authority issued in counterpart PCT Application No. PCT/EP/2012/064944 dated Nov. 2012.

* cited by examiner

*Primary Examiner* — Stephen Uyeno
(74) *Attorney, Agent, or Firm* — Silvia Salvadori, P.C.; Silvia Salvadori

(57) ABSTRACT

Disclosed are hypoallergenic variants of Mal d 1, the major allergen from *Malus domestica*, and the uses thereof in the treatment of allergic diseases.

1 Claim, 9 Drawing Sheets

A

B ced

SEQUENCE LISTING

```
<160> NUMBER OF SEQ ID NOS: 20

<210> SEQ ID NO 1
<211> LENGTH: 158
<212> TYPE: PRT
<213> ORGANISM: Malus domestica

<400> SEQUENCE: 1

Gly Val Tyr Thr Phe Glu Asn Glu Phe Thr Ser Glu Ile Pro Pro Ser
1               5                   10                  15

Arg Leu Phe Lys Ala Phe Val Leu Asp Ala Asp Asn Leu Ile Pro Lys
            20                  25                  30

Ile Ala Pro Gln Ala Ile Lys Gln Ala Glu Ile Leu Glu Gly Asp Gly
        35                  40                  45

Gly Pro Gly Thr Ile Lys Lys Ile Thr Phe Gly Glu Gly Ser Gln Tyr
    50                  55                  60

Gly Tyr Val Lys His Lys Ile Asp Ser Val Asp Glu Ala Asn Tyr Ser
65                  70                  75                  80

Tyr Ala Tyr Thr Leu Ile Glu Gly Asp Ala Leu Thr Asp Thr Ile Glu
                85                  90                  95

Lys Val Ser Tyr Glu Thr Lys Leu Val Ala Ser Gly Ser Gly Ser Ile
            100                 105                 110

Ile Lys Ser Ile Ser His Tyr His Thr Lys Gly Asp Val Glu Ile Lys
        115                 120                 125

Glu Glu His Val Lys Ala Gly Lys Glu Lys Ala His Gly Leu Phe Lys
    130                 135                 140

Leu Ile Glu Ser Tyr Leu Lys Gly His Pro Asp Ala Tyr Asn
145                 150                 155

<210> SEQ ID NO 2
<211> LENGTH: 158
<212> TYPE: PRT
<213> ORGANISM: Unknown
```

```
<220> FEATURE:
<223> OTHER INFORMATION: malus domestica - mutant

<400> SEQUENCE: 2

Gly Val Tyr Thr Phe Glu Asn Glu Phe Thr Ser Glu Ile Pro Pro Ser
1               5                   10                  15

Arg Leu Phe Lys Ala Phe Val Leu Ala Ala Asp Asn Leu Ile Pro Lys
            20                  25                  30

Ile Ala Pro Gln Ala Ile Lys Gln Ala Glu Ile Leu Glu Gly Asp Gly
        35                  40                  45

Gly Pro Gly Thr Ile Lys Lys Ile Thr Phe Gly Glu Gly Ser Gln Tyr
    50                  55                  60

Gly Tyr Val Lys His Lys Ile Asp Ser Val Asp Glu Ala Ala Tyr Ser
65              70                  75                  80

Tyr Ala Tyr Thr Leu Ile Glu Gly Asp Ala Leu Thr Asp Thr Ile Glu
            85                  90                  95

Lys Val Ser Tyr Glu Thr Lys Leu Val Ala Ser Gly Ser Gly Ser Ile
        100                 105                 110

Ile Lys Ser Ile Ser His Tyr His Thr Lys Gly Asp Val Glu Ile Lys
    115                 120                 125

Glu Glu His Val Lys Ala Gly Lys Glu Lys Ala His Gly Leu Phe Lys
130                 135                 140

Leu Ile Glu Ser Tyr Leu Lys Gly His Pro Asp Ala Tyr Asn
145                 150                 155

<210> SEQ ID NO 3
<211> LENGTH: 319
<212> TYPE: PRT
<213> ORGANISM: Unknown
<220> FEATURE:
<223> OTHER INFORMATION: Betula verrucosa - malus domestica hybrid wt

<400> SEQUENCE: 3

Gly Val Phe Asn Tyr Glu Thr Glu Thr Thr Ser Val Ile Pro Ala Ala
1               5                   10                  15

Arg Leu Phe Lys Ala Phe Ile Leu Asp Gly Asp Asn Leu Phe Pro Lys
            20                  25                  30

Val Ala Pro Gln Ala Ile Ser Ser Val Glu Asn Ile Glu Gly Asn Gly
        35                  40                  45

Gly Pro Gly Thr Ile Lys Lys Ile Ser Phe Pro Glu Gly Phe Pro Phe
    50                  55                  60

Lys Tyr Val Lys Asp Arg Val Asp Glu Val Asp His Thr Asn Phe Lys
65              70                  75                  80

Tyr Asn Tyr Ser Val Ile Glu Gly Gly Pro Ile Gly Asp Thr Leu Glu
            85                  90                  95

Lys Ile Ser Asn Glu Ile Lys Ile Val Ala Thr Pro Asp Gly Gly Ser
        100                 105                 110

Ile Leu Lys Ile Asn Asn Lys Tyr His Thr Lys Gly Asp His Glu Val
    115                 120                 125

Lys Ala Glu Gln Ile Lys Ala Ser Lys Glu Met Gly Glu Thr Leu Leu
130                 135                 140

Arg Ala Val Glu Ser Tyr Leu Leu Ala His Ser Asp Ala Tyr Asn Glu
145                 150                 155                 160

Phe Gly Val Tyr Thr Phe Glu Asn Glu Phe Thr Ser Glu Ile Pro Pro
            165                 170                 175
```

-continued

```
Ser Arg Leu Phe Lys Ala Phe Val Leu Asp Ala Asp Asn Leu Ile Pro
            180                 185                 190

Lys Ile Ala Pro Gln Ala Ile Lys Gln Ala Glu Ile Leu Glu Gly Asp
        195                 200                 205

Gly Gly Pro Gly Thr Ile Lys Lys Ile Thr Phe Gly Glu Gly Ser Gln
    210                 215                 220

Tyr Gly Tyr Val Lys His Lys Ile Asp Ser Val Asp Glu Ala Asn Tyr
225                 230                 235                 240

Ser Tyr Ala Tyr Thr Leu Ile Glu Gly Asp Ala Leu Thr Asp Thr Ile
                245                 250                 255

Glu Lys Val Ser Tyr Glu Thr Lys Leu Val Ala Ser Gly Ser Gly Ser
            260                 265                 270

Ile Ile Lys Ser Ile Ser His Tyr His Thr Lys Gly Asp Val Glu Ile
        275                 280                 285

Lys Glu Glu His Val Lys Ala Gly Lys Glu Lys Ala His Gly Leu Phe
    290                 295                 300

Lys Leu Ile Glu Ser Tyr Leu Lys Gly His Pro Asp Ala Tyr Asn
305                 310                 315
```

<210> SEQ ID NO 4
<211> LENGTH: 319
<212> TYPE: PRT
<213> ORGANISM: Unknown
<220> FEATURE:
<223> OTHER INFORMATION: betula verrucosa - malus domestica hybrid mutant

<400> SEQUENCE: 4

```
Gly Val Phe Asn Tyr Glu Thr Glu Thr Thr Ser Val Ile Pro Ala Ala
1               5                   10                  15

Arg Leu Phe Lys Ala Phe Ile Leu Asp Gly Asp Asn Leu Phe Pro Lys
            20                  25                  30

Val Ala Pro Gln Ala Ile Ser Ser Val Glu Asn Ile Glu Gly Asn Gly
        35                  40                  45

Gly Pro Gly Thr Ile Ala Lys Ile Ser Phe Pro Glu Gly Phe Pro Phe
    50                  55                  60

Lys Tyr Val Lys Asp Arg Val Asp Glu Val Asp His Thr Asn Phe Lys
65                  70                  75                  80

Tyr Asn Tyr Ser Val Ile Glu Gly Gly Pro Ile Gly Asp Thr Leu Glu
                85                  90                  95

Lys Ile Ser Asn Glu Ile Lys Ile Val Ala Thr Pro Asp Gly Gly Ser
            100                 105                 110

Ile Leu Ala Ile Asn Asn Lys Tyr His Thr Ala Gly Asp His Glu Val
        115                 120                 125

Lys Ala Glu Gln Ile Lys Ala Ser Lys Glu Met Gly Glu Thr Leu Leu
    130                 135                 140

Arg Ala Val Glu Ser Tyr Leu Leu Ala His Ser Asp Ala Tyr Asn Glu
145                 150                 155                 160

Phe Gly Val Tyr Thr Phe Glu Asn Glu Phe Thr Ser Glu Ile Pro Pro
                165                 170                 175

Ser Arg Leu Phe Lys Ala Phe Val Leu Ala Ala Asp Asn Leu Ile Pro
            180                 185                 190

Lys Ile Ala Pro Gln Ala Ile Lys Gln Ala Glu Ile Leu Glu Gly Asp
        195                 200                 205

Gly Gly Pro Gly Thr Ile Lys Lys Ile Thr Phe Gly Glu Gly Ser Gln
    210                 215                 220
```

-continued

Tyr Gly Tyr Val Lys His Lys Ile Asp Ser Val Asp Glu Ala Ala Tyr
225                 230                 235                 240

Ser Tyr Ala Tyr Thr Leu Ile Glu Gly Asp Ala Leu Thr Asp Thr Ile
                245                 250                 255

Glu Lys Val Ser Tyr Glu Thr Lys Leu Val Ala Ser Gly Ser Gly Ser
            260                 265                 270

Ile Ile Lys Ser Ile Ser His Tyr His Thr Lys Gly Asp Val Glu Ile
        275                 280                 285

Lys Glu Glu His Val Lys Ala Gly Lys Glu Lys Ala His Gly Leu Phe
        290                 295                 300

Lys Leu Ile Glu Ser Tyr Leu Lys Gly His Pro Asp Ala Tyr Asn
305                 310                 315

<210> SEQ ID NO 5
<211> LENGTH: 159
<212> TYPE: PRT
<213> ORGANISM: betula verrucosa

<400> SEQUENCE: 5

Gly Val Phe Asn Tyr Glu Thr Glu Thr Thr Ser Val Ile Pro Ala Ala
1               5                   10                  15

Arg Leu Phe Lys Ala Phe Ile Leu Asp Gly Asp Asn Leu Phe Pro Lys
            20                  25                  30

Val Ala Pro Gln Ala Ile Ser Ser Val Glu Asn Ile Glu Gly Asn Gly
        35                  40                  45

Gly Pro Gly Thr Ile Lys Lys Ile Ser Phe Pro Glu Gly Phe Pro Phe
    50                  55                  60

Lys Tyr Val Lys Asp Arg Val Asp Glu Val Asp His Thr Asn Phe Lys
65                  70                  75                  80

Tyr Asn Tyr Ser Val Ile Glu Gly Gly Pro Ile Gly Asp Thr Leu Glu
                85                  90                  95

Lys Ile Ser Asn Glu Ile Lys Ile Val Ala Thr Pro Asp Gly Gly Ser
            100                 105                 110

Ile Leu Lys Ile Asn Asn Lys Tyr His Thr Lys Gly Asp His Glu Val
        115                 120                 125

Lys Ala Glu Gln Ile Lys Ala Ser Lys Glu Met Gly Glu Thr Leu Leu
    130                 135                 140

Arg Ala Val Glu Ser Tyr Leu Leu Ala His Ser Asp Ala Tyr Asn
145                 150                 155

<210> SEQ ID NO 6
<211> LENGTH: 159
<212> TYPE: PRT
<213> ORGANISM: Unknown
<220> FEATURE:
<223> OTHER INFORMATION: betula verrucosa - mutant

<400> SEQUENCE: 6

Gly Val Phe Asn Tyr Glu Thr Glu Thr Thr Ser Val Ile Pro Ala Ala
1               5                   10                  15

Arg Leu Phe Lys Ala Phe Ile Leu Asp Gly Asp Asn Leu Phe Pro Lys
            20                  25                  30

Val Ala Pro Gln Ala Ile Ser Ser Val Glu Asn Ile Glu Gly Asn Gly
        35                  40                  45

Gly Pro Gly Thr Ile Ala Lys Ile Ser Phe Pro Glu Gly Phe Pro Phe
    50                  55                  60

```
Lys Tyr Val Lys Asp Arg Val Asp Glu Val Asp His Thr Asn Phe Lys
 65                  70                  75                  80

Tyr Asn Tyr Ser Val Ile Glu Gly Gly Pro Ile Gly Asp Thr Leu Glu
                 85                  90                  95

Lys Ile Ser Asn Glu Ile Lys Ile Val Ala Thr Pro Asp Gly Gly Ser
            100                 105                 110

Ile Leu Ala Ile Asn Asn Lys Tyr His Thr Ala Gly Asp His Glu Val
        115                 120                 125

Lys Ala Glu Gln Ile Lys Ala Ser Lys Glu Met Gly Glu Thr Leu Leu
    130                 135                 140

Arg Ala Val Glu Ser Tyr Leu Leu Ala His Ser Asp Ala Tyr Asn
145                 150                 155
```

<210> SEQ ID NO 7
<211> LENGTH: 477
<212> TYPE: DNA
<213> ORGANISM: Malus domestica

<400> SEQUENCE: 7

```
ggtgtctaca catttgagaa cgagttcacc tctgagattc caccatcaag attgttcaag      60
gcctttgtcc ttgatgctga caacctcatc cccaagattg caccccaggc aatcaagcaa     120
gctgaaatcc ttgaaggaga cggtggccct ggaaccatca aaagatcac ttttggtgaa      180
ggtagccagt acggctacgt gaagcacaag atcgactcgg ttgacgaggc aaactactca     240
tacgcctaca ctttgattga aggagatgct tgacagaca ccattgagaa ggtctcttac      300
gagaccaagt tggtggcatc tggaagtggt tccatcatca gagtatcag ccactaccac     360
accaagggtg atgttgagat caaggaagag cacgtcaagg ctggcaaaga gaaggctcat    420
ggtttgttca gcttattga gagctacctt aagggccacc ccgacgcata caactaa       477
```

<210> SEQ ID NO 8
<211> LENGTH: 480
<212> TYPE: DNA
<213> ORGANISM: betula verrucosa

<400> SEQUENCE: 8

```
ggtgttttca attacgaaac tgagaccacc tctgttatcc cagcagctcg actgttcaag      60
gcctttatcc ttgatggcga taatctcttt ccaaaggttg caccccaagc cattagcagt     120
gttgaaaaca ttgaaggaaa tggagggcct ggaaccatta agaagatcag ctttcccgaa     180
ggcttccctt tcaagtacgt gaaggacaga gttgatgagg tggaccacac aaacttcaaa     240
tacaattaca gcgtgatcga gggcggtccc ataggcgaca cattggagaa gatctccaac     300
gagataaaga tagtggcaac ccctgatgga ggttccatct gaagatcaa caacaagtac     360
cataccaaag gagaccatga ggtgaaggca agcagatta aggcaagtaa agaaatggga     420
gagacacttt tgagggccgt tgagagctac ctcttggcac actccgatgc ctacaactaa    480
```

<210> SEQ ID NO 9
<211> LENGTH: 960
<212> TYPE: DNA
<213> ORGANISM: Unknown
<220> FEATURE:
<223> OTHER INFORMATION: betula verrucosa - malus domestica hybrid

<400> SEQUENCE: 9

```
ggtgttttca attacgaaac tgagaccacc tctgttatcc cagcagctcg actgttcaag      60
gcctttatcc ttgatggcga taatctcttt ccaaaggttg caccccaagc cattagcagt     120
```

```
gttgaaaaca ttgaaggaaa tggagggcct ggaaccatta agaagatcag ctttcccgaa    180
ggcttcsctt tcaagtacgt gaaggacaga gttgatgagg tggaccacac aaacttcaaa    240
tacaattaca gcgtgatcga gggcggtccc ataggcgaca cattggagaa gatctccaac    300
gagataaaga tagtggcaac ccctgatgga ggttccatct tgaagatcaa caacaagtac    360
cataccaaag agaccatga ggtgaaggca gagcagatta aggcaagtaa agaaatggga    420
gagacacttt tgagggccgt tgagagctac ctcttggcac actccgatgc ctacaacgaa    480
ttcggtgtct acacatttga gaacgagttc acctctgaga ttccaccatc aagattgttc    540
aaggcctttg tccttgatgc tgacaacctc atccccaaga ttgcacccca ggcaatcaag    600
caagctgaaa tccttgaagg agacggtggc cctggaacca tcaaaaagat cacttttggt    660
gaaggtagcc agtacggcta cgtgaagcac aagatcgact cggttgacga ggcaaactac    720
tcatacgcct acactttgat tgaaggagat gctttgacag acaccattga aggtctctct    780
tacgagacca agttggtggc atctggaagt ggttccatca tcaagagtat cagccactac    840
cacaccaagg gtgatgttga gatcaaggaa gagcacgtca aggctggcaa agagaaggct    900
catggtttgt tcaagcttat tgagagctac cttaagggcc accccgacgc atacaactaa    960

<210> SEQ ID NO 10
<211> LENGTH: 477
<212> TYPE: DNA
<213> ORGANISM: Unknown
<220> FEATURE:
<223> OTHER INFORMATION: malus domestica - mutant

<400> SEQUENCE: 10
ggtgtctaca catttgagaa cgagttcacc tctgagattc caccatcaag attgttcaag     60
gcctttgtcc ttgctgctga caacctcatc cccaagattg caccccaggc aatcaagcaa    120
gctgaaatcc ttgaaggaga cggtggccct ggaaccatca aaaagatcac ttttggtgaa    180
ggtagccagt acggctacgt gaagcacaag atcgactcgg ttgacgaggc agcctactca    240
tacgcctaca ctttgattga aggagatgct ttgacagaca ccattgagaa ggtctcttac    300
gagaccaagt tggtggcatc tggaagtggt tccatcatca agagtatcag ccactaccac    360
accaagggtg atgttgagat caaggaagag cacgtcaagg ctggcaaaga gaaggctcat    420
ggtttgttca agcttattga gagctacctt aagggccacc ccgacgcata caactaa      477

<210> SEQ ID NO 11
<211> LENGTH: 158
<212> TYPE: PRT
<213> ORGANISM: Unknown
<220> FEATURE:
<223> OTHER INFORMATION: malus domestica - mutant

<400> SEQUENCE: 11

Gly Val Tyr Thr Phe Glu Asn Glu Phe Thr Ser Glu Ile Pro Pro Ser
1               5                   10                  15

Arg Leu Phe Lys Ala Phe Val Leu Asp Ala Asp Asn Leu Ile Pro Lys
            20                  25                  30

Ile Ala Pro Gln Ala Ile Lys Gln Ala Glu Ile Leu Glu Gly Asp Gly
        35                  40                  45

Gly Pro Gly Thr Ile Lys Lys Ile Thr Phe Gly Glu Gly Ser Gln Tyr
    50                  55                  60

Gly Tyr Val Lys His Lys Ile Asp Ser Val Asp Glu Ala Ala Tyr Ser
65                  70                  75                  80
```

```
Tyr Ala Tyr Thr Leu Ile Glu Gly Asp Ala Leu Thr Asp Thr Ile Glu
                85                  90                  95

Lys Val Ser Tyr Glu Thr Lys Leu Val Ala Ser Gly Ser Gly Ser Ile
            100                 105                 110

Ile Lys Ser Ile Ser His Tyr His Thr Lys Gly Asp Val Glu Ile Lys
        115                 120                 125

Glu Glu His Val Lys Ala Gly Lys Glu Lys Ala His Gly Leu Phe Lys
    130                 135                 140

Leu Ile Glu Ser Tyr Leu Lys Gly His Pro Asp Ala Tyr Asn
145                 150                 155

<210> SEQ ID NO 12
<211> LENGTH: 27
<212> TYPE: DNA
<213> ORGANISM: Unknown
<220> FEATURE:
<223> OTHER INFORMATION: oligonucleotide

<400> SEQUENCE: 12
gcctttgtcc ttgctgctga caacctc                                      27

<210> SEQ ID NO 13
<211> LENGTH: 27
<212> TYPE: DNA
<213> ORGANISM: Unknown
<220> FEATURE:
<223> OTHER INFORMATION: oligonucleotide

<400> SEQUENCE: 13
gttgacgagg cagcctactc atacgcc                                      27

<210> SEQ ID NO 14
<211> LENGTH: 22
<212> TYPE: DNA
<213> ORGANISM: Unknown
<220> FEATURE:
<223> OTHER INFORMATION: oligonucleotide

<400> SEQUENCE: 14
ggtgttttca attacgaaac tg                                           22

<210> SEQ ID NO 15
<211> LENGTH: 24
<212> TYPE: DNA
<213> ORGANISM: Unknown
<220> FEATURE:
<223> OTHER INFORMATION: oligonucleotide

<400> SEQUENCE: 15
gcgaattcgt tgtaggcatc ggag                                         24

<210> SEQ ID NO 16
<211> LENGTH: 31
<212> TYPE: DNA
<213> ORGANISM: Unknown
<220> FEATURE:
<223> OTHER INFORMATION: oligonucleotide

<400> SEQUENCE: 16
cgcgaattcg gtgtctacac atttgagaac g                                 31
```

<210> SEQ ID NO 17
<211> LENGTH: 30
<212> TYPE: DNA
<213> ORGANISM: Unknown
<220> FEATURE:
<223> OTHER INFORMATION: oligonucleotide

<400> SEQUENCE: 17
gcgggatcct tagttgtatg cgtcggggtg                                30

<210> SEQ ID NO 18
<211> LENGTH: 55
<212> TYPE: DNA
<213> ORGANISM: Unknown
<220> FEATURE:
<223> OTHER INFORMATION: oligonucleotide

<400> SEQUENCE: 18
gcgggtaccc atatgcatca ccatcaccat cacggtgttt tcaattacga aactg     55

<210> SEQ ID NO 19
<211> LENGTH: 960
<212> TYPE: DNA
<213> ORGANISM: Unknown
<220> FEATURE:
<223> OTHER INFORMATION: betula verrucosa - malus domestica hybrid
      mutant

<400> SEQUENCE: 19
ggtgttttca attacgaaac tgagaccacc tctgttatcc cagcagctcg actgttcaag     60
gcctttatcc ttgatggcga taatctcttt ccaaaggttg caccccaagc cattagcagt    120
gttgaaaaca ttgaaggaaa tggagggcct ggaaccattg cgaagatcag ctttcccgaa    180 ggcttcccctt tcaagtacgt gaaggacaga gttgatgagg tggaccacac aaacttcaaa    240
tacaattaca gcgtgatcga gggcggtccc ataggcgaca cattggagaa gatctccaac    300
gagataaaga tagtggcaac ccctgatgga ggttccatct ggcgatcaa caacaagtac    360 cataccgcag agaccatgga ggtgaaggca gagcagatta aggcaagtaa agaaatggga    420
gagacacttt tgagggccgt tgagagctac ctcttggcac actccgatgc ctacaacgaa    480
ttcggtgtct acacatttga gaacgagttc acctctgaga ttccaccatc aagattgttc    540
aaggcctttg tccttgctgc tgacaacctc atccccaaga ttgcaccccca ggcaatcaag    600 caagctgaaa tccttgaagg agacggtggc cctggaacca tcaaaaagat cacttttggt    660
gaaggtagcc agtacggcta cgtgaagcac aagatcgact cggttgacga ggcagcctac    720
tcatacgcct acactttgat tgaaggagat gctttgacag acaccattga aaggtctct    780 tacgagacca agttggtggc atctggaagt ggttccatca tcaagagtat cagccactac    840
cacaccaagg gtgatgttga gatcaaggaa gagcacgtca aggctggcaa agagaaggct    900
catggtttgt tcaagcttat tgagagctac cttaagggcc accccgacgc atacaactaa    960

<210> SEQ ID NO 20
<211> LENGTH: 480
<212> TYPE: DNA
<213> ORGANISM: Unknown
<220> FEATURE:
<223> OTHER INFORMATION: betula verrucosa mutant

<400> SEQUENCE: 20
ggtgttttca attacgaaac tgagaccacc tctgttatcc cagcagctcg actgttcaag     60
gcctttatcc ttgatggcga taatctcttt ccaaaggttg caccccaagc cattagcagt    120

```
gttgaaaaca ttgaaggaaa tggagggcct ggaaccattg cgaagatcag ctttcccgaa     180
ggcttccctt tcaagtacgt gaaggacaga gttgatgagg tggaccacac aaacttcaaa     240
tacaattaca gcgtgatcga gggcggtccc ataggcgaca cattggagaa gatctccaac     300
gagataaaga tagtggcaac ccctgatgga ggttccatct tggcgatcaa caacaagtac     360
cataccgcag gagaccatga ggtgaaggca gagcagatta aggcaagtaa agaaatggga     420 gagacactttt tgagggccgt tgagagctac ctcttggcac actccgatgc ctacaactaa   480
```

HYPOALLERGENIC VARIANTS OF MAL D 1, THE MAJOR ALLERGEN FROM MALUS DOMESTICA This application is a U.S. national stage of PCT/EP2012/064944 filed on Jul. 31, 2012, which claims priority to and the benefit of Italian Application No. MI2011A001489 filed on Aug. 3, 2011, the contents of which are incorporated herein by reference in their entirety.

The present invention relates to hypoallergenic sequence variants of the Mal d 1 protein, nucleic acid molecules encoding for them, pharmaceutical compositions containing them, and their use in the immunotherapy of allergic diseases caused by the species *Malus domestica*.

BACKGROUND TO THE INVENTION

Allergies are caused by a dysfunction in the immune system, which reacts to harmless proteins, mainly contained in pollens, mites, epithelia and foodstuffs, by producing IgE-class antibodies.

Recent estimates indicate that over 25% of the population of the industrialised countries suffers from this diseases which, if it persists, can lead to a deterioration in the symptoms (e.g. appearance of asthma) and sensitisation to other allergens, thus complicating the choice of the most suitable treatment.

About a third of all the allergic subjects in the world are allergic to tree pollen. In temperate regions, pollen from trees belonging to the order Fagales (birch, alder, hazel, oak and hornbeam) is one of the major causes of allergic asthma and rhinitis. About 95% of patients allergic to birch pollen produce IgE antibodies against Bet v 1, and 60% of these patients only react to Bet v 1 (cDNA deposited at GenBank acc. no. X15877), the major allergen of birch pollen (1).

A high percentage of individuals allergic to birch pollen (50%-93%) develop allergic reactions after eating certain foods (apples, carrots, hazelnuts and celery). This type of hypersensitivity in patients with birch pollen allergy, characterised by allergy to fruit, nuts and vegetables, is described as "pollen-food syndrome" (PFS). The symptoms range from reactions of the mucosa of the upper digestive tract (oral allergy syndrome) and the gastroenteric tract to urticaria and asthma, and in some cases can cause anaphylactic shock. Adverse reactions to fruit occur most frequently with apple. In the case of pollinosis caused by birch pollen, this syndrome is mainly mediated by cross-reacting IgE antibodies originally induced by Bet v 1 (2).

The treatment of these patients is mainly based on food allergen avoidance from the diet. For the treatment of allergy to pollens, animals and mites, hyposensitizing specific immunotherapy (SIT), unlike pharmacological treatment, has proved to be an effective form of etiological treatment, which positively affects some immunological parameters that are the basis of the disease. SIT involves administering increasing doses of standardised extracts (vaccines) obtained from the substance that causes the disease (3). In this way a kind of "immunological tolerance" against that substance is gradually induced in the patient, accompanied by a reduction in, if not the disappearance of, the allergy symptoms. Conversely, specific immunotherapy is not commonly used to treat food allergies in view of the high risk of inducing serious side effects, including anaphylactic shock.

Although the cross-reactivity between Bet v 1 and homologous food proteins underlies the reactions induced by PFS, it has been found that SIT with birch pollen does not induce any improvement in food allergy symptoms.

This inefficacy has been observed in the case of carrot allergy, mainly caused by the allergen Dau c 1, a homologue of Bet v 1, in which primary sensitisation arises towards the birch allergen and subsequent sensitisation, after eating carrot, towards new epitopes of Dau c 1 which do not cross-react with Bet v 1 (4).

In the treatment of apple allergy, SIT with birch pollen extract gave rise to controversial, sometimes favourable results, probably due to the greater sequence identity between Bet v 1 and Mal d 1 (60% of the amino-acid sequence, as against 40% for Dau c 1).

In a 1998 study, in 84% of patients allergic to birch and apple who were treated with SIT based on birch pollen extract, a significant reduction (50-95%) or total disappearance of OAS (oral allergy syndrome) symptoms after eating apple had already disappeared after the first year's treatment (5). In a more recent study, published in 2004, SIT with birch pollen extract led to a significant reduction in SPT reactivity to Bet v 1 and Mal d 1 after only three months' treatment. The IgG4 antibodies strongly induced against Bet v 1 exhibited cross-reactivity to Mal d 1, thus supporting the hypothesis that SIT against birch pollen allergy can also reduce allergy to foods containing Bet v 1 homologous allergens (6). Another study published in the same year (2004) showed, in patients allergic to birch and apple, that SIT based on birch pollen extract significantly improved the allergic symptoms caused by pollen, but did not reduce the severity of apple allergy (7).

On the basis of current knowledge, it therefore cannot be stated with certainty that immunotherapy with birch pollen allergens provides significant benefits in the case of allergy to foods containing Bet v 1 homologues, which should therefore be treated as a separate disease.

One of the allergens most frequently involved in PFS cross-reactivity to Bet v 1 is Mal d 1, the major allergen of apple, a fruit belonging to the Rosaceae family. Mal d 1 shares approximately 60% of its amino-acid sequence with Bet v 1 (identity), and cross-reactivity experiments have demonstrated the presence of common IgE and T epitopes (8,9).

Mal d 1 (Acc. No. Q9SYW3 or No AJ417551) is a 159 amino-acid protein with a molecular weight of 17.7 kDa. (10). This allergen belongs to the PR-10 family of "pathogenesis related proteins", i.e. ubiquitous proteins produced by plants in response to environmental or biological stresses, the function of which is believed to be connected with steroid transport. Mal d 1 is located in both the peel and the pulp of apples. Measurement of Mal d 1 content in protein extracts from numerous varieties of apple demonstrate that this allergen is present in considerably different concentrations in the different varieties; variability in the content of Mal d 1 was also found in the same variety grown in different places. Moreover, even in varieties with a low Mal d 1 content, it has been observed that the allergen concentration increases significantly during ripening and storage of the fruit.

Mal d 1 is represented by a gene family with at least eighteen members, characterised by the presence or absence of introns in the gene. Some members are highly conserved in the different apple varieties (Mal d 1.01, Mal d 1.02), while others present more variability (Mal d 1.04, Mal d 1.05, Mal d 1.06 A, B, C) (11). When SPT analysis was conducted on patients with pollen-food syndrome, an association between the protein variants encoded by genes Mal d 1.04 and Mal d 1.06 A and greater allergenicity of the apple varieties was observed. The results of this type of study may have applications in the identification and cultivation of apple varieties with lower allergenicity for use as a food or as raw material for conventional immunotherapy.

The development of hypoallergenic food allergens for use in specific immunotherapy may represent a good alternative to food allergen avoidance and allow the treatment of a disease which, as well as involving high risks for patients' health, has a significant negative impact on quality of life and can cause incapacitating nutritional imbalances.

In recent years, a great deal of attention has focused on developing safer, more effective vaccines, consisting of recombinant proteins mutagenised at the level of amino acids important for IgE binding, namely hypoallergenic variants that favourably influence the natural progression of the disease without causing adverse effects (12).

Some studies of hypoallergenic variants of Mal d 1 or homologous proteins from other fruit belonging to the Rosaceae family are available in the literature.

On the basis of the cross-reactivity between Bet v 1 and Mal d 1, a mutant of Mal d 1, the major apple allergen, was produced by site-directed mutagenesis of five amino acid residues on isoform Mal d 1.0108 (T10P; I30V, T57N, T112C and I113V) selected by analogy with a hypoallergenic mutant of Bet v 1 allergen (9). The substitution of said amino acids reduced the allergenic activity of Mal d 1 by 90%, as demonstrated by SPT and DBPCFC (double-blind placebo-controlled food challenge) analysis. The same mutant with five amino-acid substitutions was tested in parallel with the analogous mutant of Bet v 1 and with the corresponding wild-type molecules (13). Although the sera of patients allergic to birch and apple exhibited greater IgE reactivity against Bet v 1 in immunoblotting tests, a reduction in binding to both the mutants tested was observed. In ELISA assays, in the majority of sera tested (10/14), a reduction from 30 to 88% in the IgE-binding of mutant Mal d 1 was observed compared to the wild-type allergen. However, the mutagenesis of the five amino acids selected does not seem to prejudice the IgE reactivity of the main epitopes of Mal d 1, as no variation in specific IgE binding was observed in some of the sera analysed (3/14).

In Pru av 1, the major cherry allergen homologous to Mal d 1, punctiform substitution of serine 112 proved critical for recognition of the molecule by IgEs. The mutagenesis of the same amino acid in proline in homologue Bet v 1 confirmed the importance of serine 112 in preserving the structure of the cross-reactive IgE epitope. The substitution of Glu45 by tryptophan in the P-loop sequence of Pru av 1 demonstrated that this region is an IgE epitope cross-reactive to Bet v 1 (14). Three other Pru av 1 variants were obtained by mutagenesis of amino acids in position 28 (Asn28Lys), 108 (Pro108Ala), or both. Reduced IgE binding in up to 80% of sera from patients allergic to birch and cherry was observed for the single mutant (Asn28Lys) and the double mutant (Asn28Lys, Pro108Ala), whereas a reduction in only 12% was obtained for the single mutant on Pro108, suggesting that amino acid Asn28 in Pru av 1 is involved in an IgE epitope. This asparagine is exposed to the solvent, and is part of one of the areas proposed as the main antigen sites in homologous protein Bet v 1 (15).

The study of the three-dimensional structure of Bet v 1 by NMR analysis and X-ray diffraction led to the identification of three zones with an area exceeding 600 Å which may be involved in IgE binding (16). These three zones exposed on the surface consist of highly conserved amino acids in the homologous allergens expressed in species belonging to the order Fagales, and have been proposed as potential IgE epitopes responsible for the cross-reactivity between Bet v 1 and the homologous proteins of plant pollens. Site-directed mutagenesis of amino acids in these areas confirmed their involvement in IgE binding. The mutations in Bet v 1 that characterise the two multiple mutants (T28, Q32, S45, G108) and (V5, S42, S45, K78, V103, I123, E134, H156, N160), for example, modify up to five different areas distributed on the molecular surface, including the three zones described above, and cause a reduction in allergenicity (17). The amino-acid sequences that constitute the three IgE epitopes proposed by Gajhede are also conserved in the food allergens homologous to Bet v 1. In order to reduce surface similarity to Bet v 1, the conserved amino acids Thr 28, Gln 32 and Ser 45 of Mal d 1, located in one of the areas described above, were substituted with amino acids not present in Bet v 1 in the corresponding positions. The substitution of these residues did not vary the ability of mutant Mal d 1 to inhibit IgE-Bet v 1 binding compared with the wt counterpart, while histamine release was abolished in basophils from the blood of the same birch allergic patients in only one case out of the five tested (24).

In order to identify the IgE epitopes involved in the clinical symptoms of pollen-food syndrome, a chimeric protein was generated by grafting four short peptide stretches of Mal d 1 onto Bet v 1 sequence (18). The transplanted regions included the amino acid residues previously proved crucial for patients' IgE binding to both allergens, Bet v 1 and Mal d 1: T10, F30, S57, S112, I113 and D125. The IgE reactivity of the chimeric protein was tested using sera from two groups of patients with birch allergy, without PFS or showing PFS symptoms following apple ingestion. The chimeric molecule was recognised by the IgEs of both groups, but binding was significantly lower in the group with no PFS compared to patients with apple allergy, suggesting that the grafted sequences on Bet v 1 were involved in Bet v 1/Mal d 1 IgE cross-reactivity.

The birch pollen allergy characterised by PFS represents an excellent study model for identifying cross-reacting IgE epitopes and allowing the production of recombinant allergens with a reduced IgE binding capacity.

The possibility to use engineered multimeric molecules consisting of different allergens from the same organism or different organisms for specific hyposensitizing therapy has long been considered fascinating. This approach allows a number of allergens to be assembled in a single molecule with the advantage of producing a single preparation containing the allergens in a precise molar ratio. The association of Bet v 1 and Mal d 1 in a single hybrid molecule should represent the T-epitope repertoire of both molecules, and may induce a strong IgG protective response (17) against both allergens. Induction of IgG antibodies specific for the sensitising allergen is one of the factors correlated with the benefit induced by SIT. Such (protecting) antibodies can inhibit the IgE binding to the antigen, altering the tridimensional conformation of the molecule.

Some studies have been conducted to investigate the clinical effects on birch pollen allergy of SIT with trimeric derivatives of the allergen Bet v 1 (19). The treatment induced strong IgG1 and IgG4 specific allergen antibody response and reduced nasal and skin reactivity, but did not yield to a significant improvement in clinical symptoms.

Significant IgG antibody response was also observed in experiments in mice treated with the dimeric wt or mutant form in position 112 of carrot allergen Dau c 1, homologous to Bet v 1 allergen (20). Both dimeric variants proved more antigenic than the mixture of the corresponding monomeric forms. Moreover, all the murine sera produced against Dau c 1 (in monomeric, dimeric, wt and mutant form) contained specific antibodies cross-reacting to epitopes recognised by human IgE, indicating that structurally altered antigens like dimers are able to induce the production of antibodies specific for conformational epitopes.

The use of a hypoallergenic hybrid variant like Bet v 1-Mal d 1 may eliminate the difficulties caused by severe adverse reactions to food allergens and improve a tolerogenic response not only to Bet v 1, as occurs when SIT with birch pollen extract is used, but also to the major allergen of apple.

DESCRIPTION OF THE INVENTION

It has now been found that binding of Mal d 1 allergen to IgE can be reduced by modifying its sequence through substitution of specific amino-acid residues.

According to a first aspect thereof, the invention provides a sequence variant of Mal d 1 obtained from the major allergen of *Malus domestica*, Mal d 1 (wt sequence SEQ ID NO:1), or an isoform thereof having at least 95% sequence identity with SEQ ID NO:1, preferably at least 97%, the said variant being characterised by:
  a) reduced reactivity to IgE compared to wild-type Mal d 1 SEQ ID NO:1;
  b) an amino-acid sequence which, when aligned with SEQ ID NO:1, presents at least one, and preferably two substitutions in the Asp and/or Asn residues in positions 25 and 78 of SEQ ID NO: 1 or in the corresponding positions of said isoforms of Mal d 1.

The isoforms of Mal d 1 having at least 95% sequence identity with SEQ ID NO:1 include the natural sequences deposited at accession numbers Mal d 1.0201 (Uniprot Q40280) and Mal d 1.0204 (Uniprot Q9SYV4).

The preferred variants of allergen Mal d 1 are those wherein residue Asp 25 is substituted with a neutral, polar or basic amino acid, which is preferably selected from Ala, Thr, Gly, Pro, Leu, Ile, Ser, Phe, Lys and Arg, and more preferably from Ala, Thr, Ser, Gly, Lys and Arg, while residue Asn 78 is substituted with a neutral, acid or basic amino acid, which is preferably selected from Ala, Gly, Pro, Leu, Ile, Phe, Lys, Arg, Asp and Glu, and more preferably from Ala, Gly, Lys, Arg, Asp and Glu.

In a preferred embodiment, the variant according to the invention bearing 2 substitutions has the sequence identified in SEQ ID NO: 2.

The substitution variant of allergen Mal d 1 according to the present invention shows an IgE reactivity reduction by at least 10% compared with the wild-type molecule, preferably by at least 50%, and more preferably by at least 80%, to the serum of patients allergic to *Betula verrucosa* pollen and apple.

Figure 1:
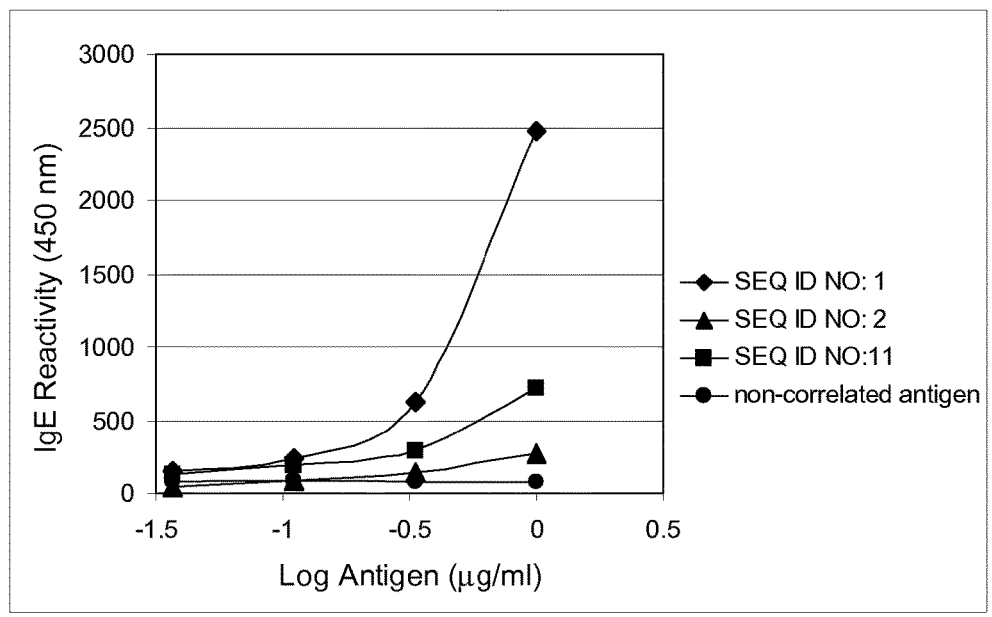
FIG. 1 shows IgE reactivity of variant SEQ ID NO: 2.

The IgE reactivity of variant SEQ ID NO: 2 was analysed in a pool of sera from allergic individuals by ELISA assay (FIG. 1). When incubated with a pool of sera from patients allergic to birch pollen and apple, said variant presented a reduction in IgE reactivity (to 1 µg/ml), compared with wt allergen Mal d 1 (SEQ ID NO: 1), of 89% (SEQ ID NO: 2). Another example of a variant of Mal d 1 allergen with a substitution, Asn 78 in Ala (SEQ ID NO:11), exhibited a 70.9% reduction in IgE binding under the same conditions (FIG. 1).

Figure 2:
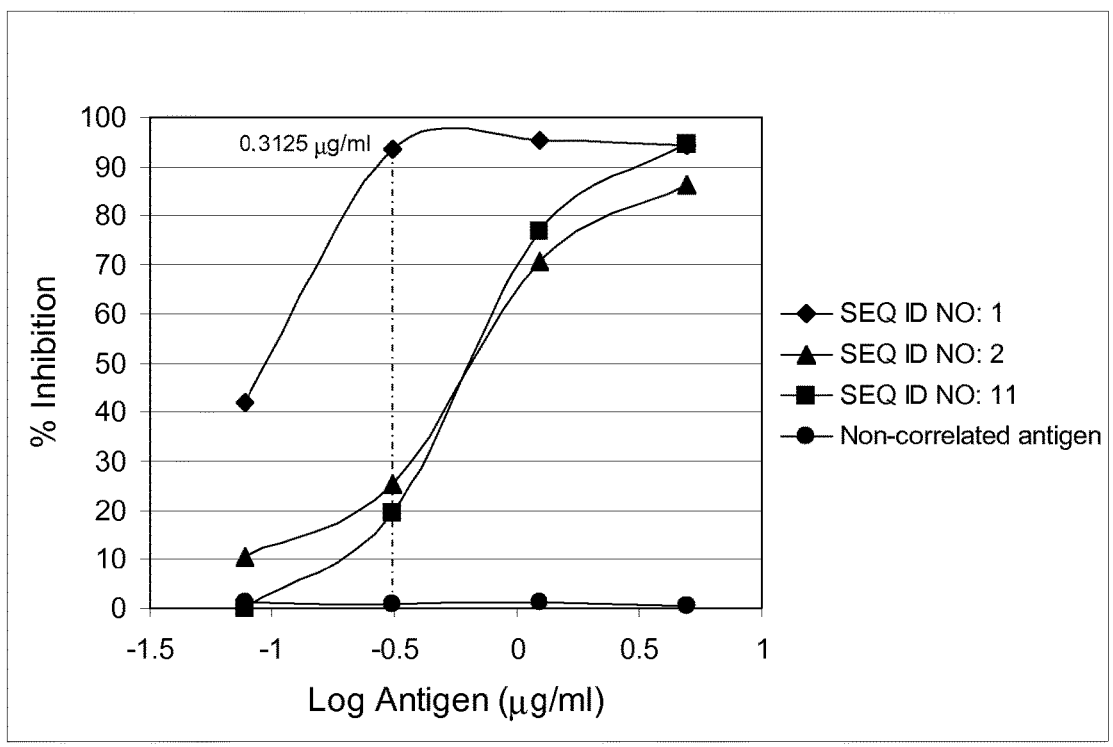
FIG. 2 shows the reactivity of homologous epitopes from different proteins.

These results were confirmed by ELISA-inhibition experiments, which allow to evaluate the reactivity of homologous epitopes from different proteins. It was found that with 0.3125 µg/ml of inhibitor, binding of the wt Mal d 1 protein (SEQ ID NO: 1) to IgEs from a pool of sera is inhibited by 93.3% when the serum is pre-treated with the same protein, and by 25.4% when pre-incubated with variant SEQ ID NO: 2 (FIG. 2). Under the same conditions, the variant with single substitution in Asn78 inhibits SEQ ID NO:1-IgE binding by 19.7% (FIG. 2, SEQ ID NO: 11).

These results clearly indicate that substitution of amino acids in position 25 and/or 78 of SEQ ID NO: 1 interferes with the recognition of Mal d 1 allergen by IgEs.

Figure 3:
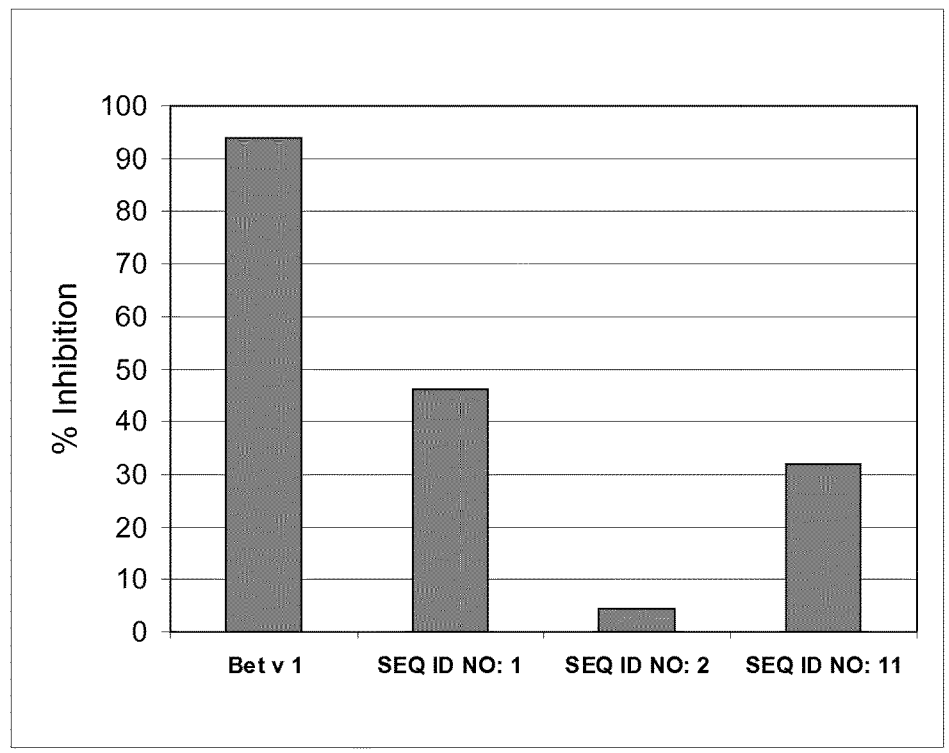
FIG. 3 shows the inhibition of the binding of wt Bet v 1 to IgEs.

It has also been observed that the allergen wt Mal d 1 SEQ ID NO: 1 and the hypoallergenic variant SEQ ID NO: 2, used at the concentration of 0.625 µg/ml, inhibit binding of wt Bet v 1 to IgEs from a pool of birch- and apple-positive sera by different degrees of efficacy. Inhibition amounts to 94% when the serum is pre-treated with the same protein wt Bet v 1, 46% when pre-incubated with protein SEQ ID NO: 1, 4.2% with SEQ ID NO: 2, and 32.1% when the serum is pre-treated with the single substitution variant SEQ ID NO: 11 (FIG. 3).

Figure 4:
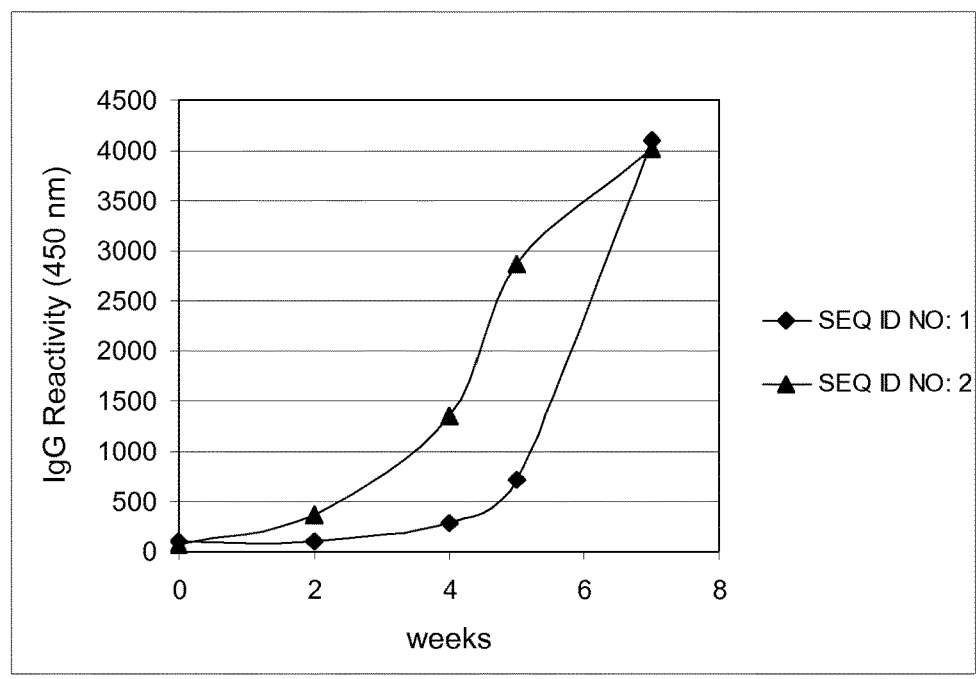
FIG. 4 shows specific IgG response from mice immunized with wt Mal d 1 allergen SEQ ID NO: 1 and with the hypoallergenic variant SEQ ID NO: 2.
Figure 5:
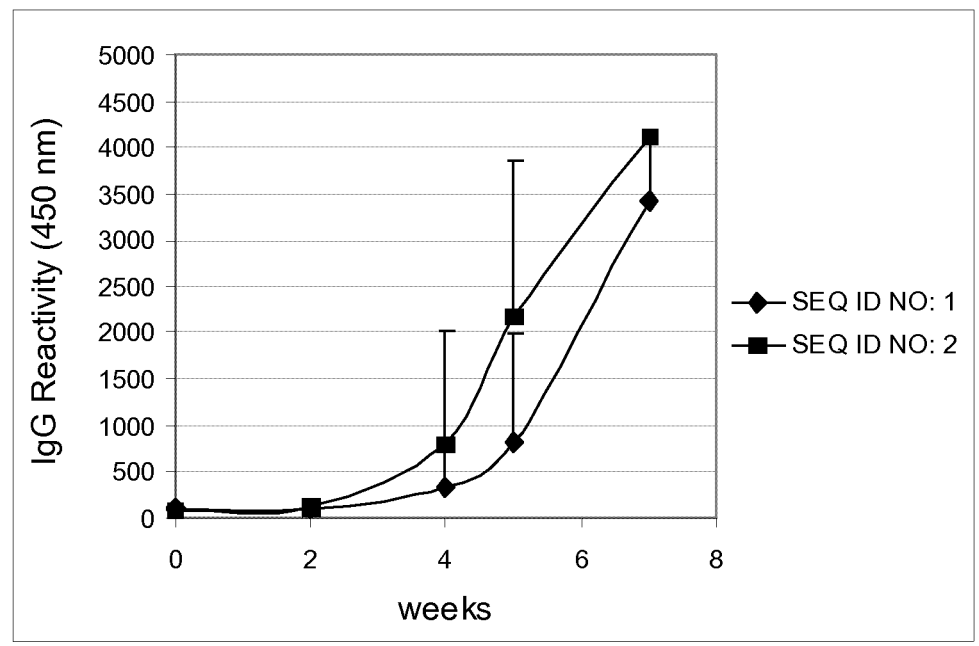
FIG. 5 shows specific IgG response induced by wt Mal d 1 allergen SEQ ID NO: 1 and by the hypoallergenic variant SEQ ID NO: 2.

Wt Mal d 1 allergen SEQ ID NO: 1 and the hypoallergenic variant SEQ ID NO: 2, used to immunise Balb/c mice, induce a specific IgG response (FIG. 4). In particular, the antibodies produced against SEQ ID NO: 2 also recognise the wt counterpart SEQ ID NO: 1 (FIG. 5), demonstrating that modification of the residues in position 25 and 78 does not cause a significant alteration in the IgG epitopes of the molecule. Moreover, immunisation with variant SEQ ID NO: 2 induces a higher and faster immune response than that obtained with the wt counterpart SEQ ID NO:1. Conversely, the antibodies present in the serum of animals immunised with an unrelated antigen are unable to recognise wt Mal d 1 and SEQ ID NO: 2.

Figure 6:
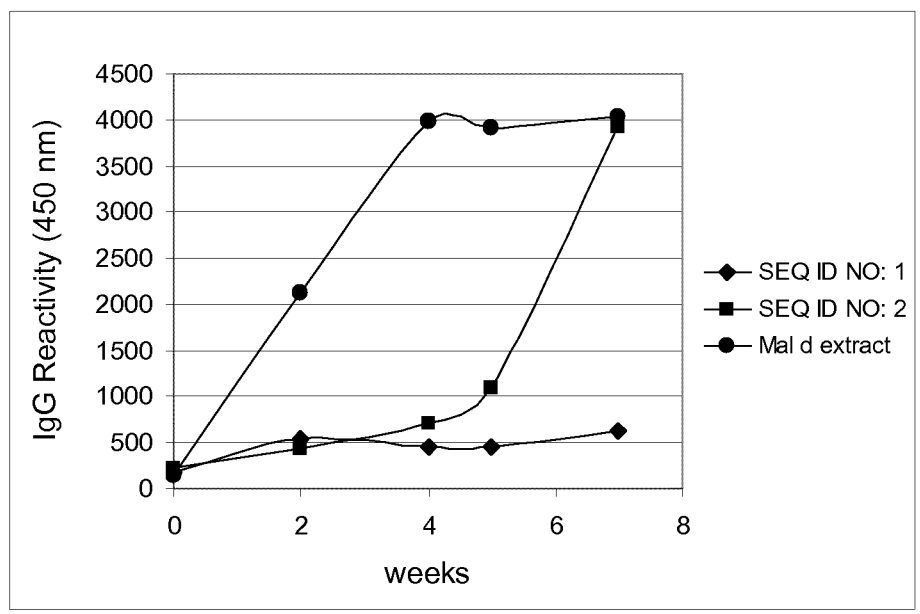
FIG. 6 shows reactivity to apple extract by the antibodies induced by immunizing mice with SEQ ID NO: 2.

Reactivity to apple extract by the antibodies induced by immunising mice with SEQ ID NO: 2 is detectable from the fifth week, and peaks in the seventh week, when very weak recognition by the antibodies produced by immunising with SEQ ID NO: 1 is observed, although the antibody titre towards wt Mal d 1 at seven weeks is comparable with that obtained in mice immunised with SEQ ID NO: 2 (FIG. 6).

Figure 7:
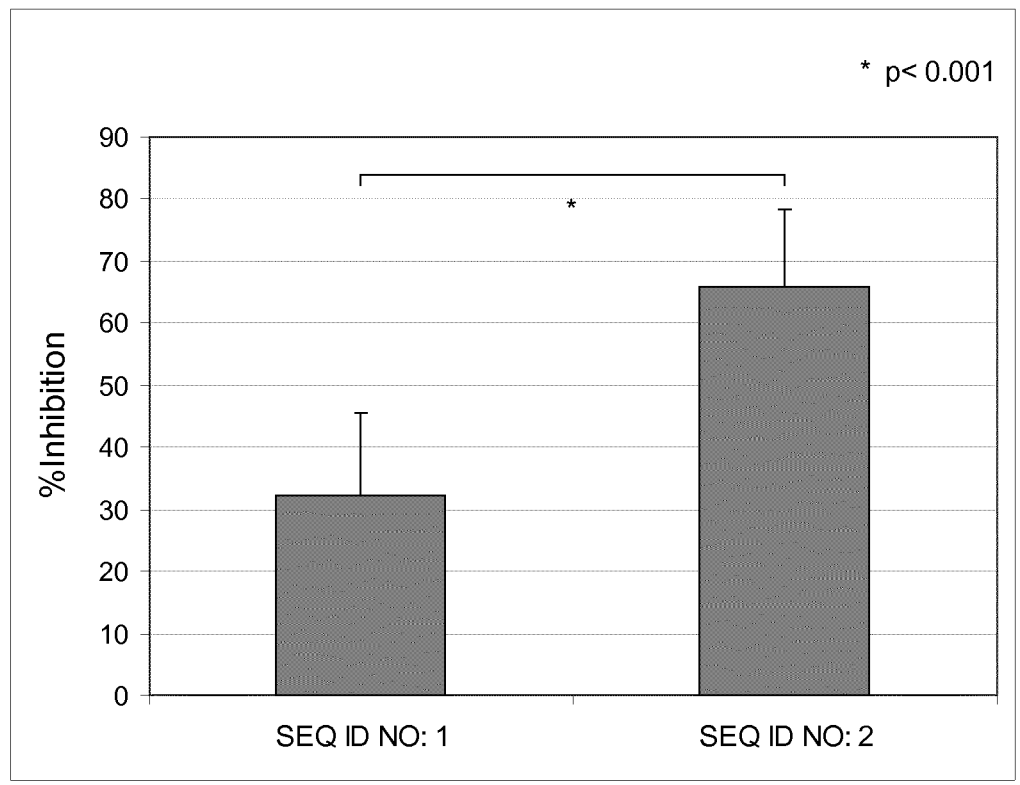
FIG. 7 shows IgG antibodies produced against SEQ ID NO: 2 inhibiting binding of Mal d 1.

Concerning the induction of protective antibodies able to compete in binding between allergen and IgE, it has been observed that the IgG antibodies produced against SEQ ID NO: 2 inhibit the binding of Mal d 1 (SEQ ID No. 1) to IgEs of patients allergic to birch and apple more effectively than the wt protein (SEQ ID NO: 1) ($p<0.001$) (FIG. 7). ELISA inhibition experiments have demonstrated that the IgGs from mice immunised with SEQ ID NO: 2 inhibits the IgE reactivity of seven patients sera by an average of 66% (with values ranging from 49.6 to 82.2%), and those produced against SEQ ID NO: 1 by 32.3% (11.5-53%). The serum of the non-immunised animals used as control does not give rise to any inhibition of specific IgE-Mal d 1 binding.

A further aspect of the present invention relates to an immunologically active peptide corresponding to a Mal d 1 fragment containing at least one of the substitutions described above. Said peptide preferably contains 15 to 35, and more preferably 15 to 20, amino-acid residues. As used herein, the expression "immunologically active" means that the peptide must be able to stimulate an IgE-independent immune response.

Another aspect of the invention relates to a hybrid protein containing a sequence variant of the major allergen of *Malus domestica* as described herein and a hypoallergenic variant of the Bet v 1 major allergen of *Betula verrucosa* pollen, possibly separated by a linker.

Figure 8:
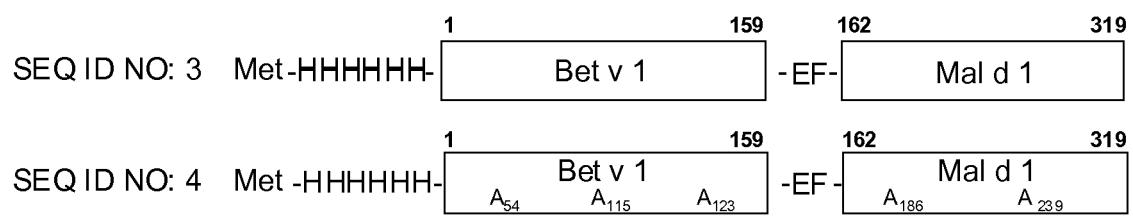
FIG. 8 shows that the amino-terminus of the hybrid protein is occupied by Bet v 1 and the carboxy-terminus by Mal d 1.

In the hybrid protein according to the invention, said hypoallergenic variants of Mal d 1 and Bet v 1 are indifferently positioned at the amino or carboxy-terminus with head-to-tail orientation; in other words, when the amino-terminus of the hybrid protein coincides with the amino-terminus of Bet v 1 or Mal d 1, the carboxy-terminus of the hybrid protein coincides with the carboxy-terminus of protein Mal d 1 or Bet v 1 respectively. According to a preferred embodiment, the amino-terminus of the hybrid protein is occupied by Bet v 1, and the carboxy-terminus by Mal d 1 (FIG. 8).

The linker that separates the mutated sequences of Bet v 1 and Mal d 1 preferably consists of a chain of 8 amino acids, more preferably a chain of two amino acids, and even more preferably of dipeptide EF (Glu-Phe).

In a preferred embodiment of the invention, the hybrid protein contains the hypoallergenic variant of Bet v 1 described in international patent application WO2007/073907 and European patent application EP2172215, filed by the same applicant and entirely incorporated here by reference. In particular, the hypoallergenic variant of Bet v 1 contained in the hybrid protein according to the invention is obtained from a protein of sequence SEQ ID NO:5 or an isoform thereof which is at least 94%, and preferably at least 97% identical to said sequence SEQ ID NO:5, by substituting the Lys residues in position 54, 115 and/or 123 (in the case of SEQ ID NO:5), or in the corresponding positions of said isoform, with neutral or polar amino acids selected from Ala, Thr, Gly, Pro, Leu, Ile, Phe and Ser. In a preferred embodiment, said hypoallergenic variant of Bet v 1 is SEQ ID NO:6. The hypoallergenic variants of Bet v 1 referred to here are described in the two patent applications cited above.

The isoforms of Bet v 1 having over 94% sequence identity with SEQ ID NO:5 include the natural molecules deposited under accession numbers Bet v 1-a (Uniprot P15494), Bet v 1-j (Uniprot P43184) and Bet v 1-f (Uniprot P43179).

The hybrid protein of sequence SEQ ID NO:4 wherein the hypoallergenic variant of Bet v 1 (SEQ ID NO: 6) binds to the hypoallergenic variant of Mal d 1 (SEQ ID NO:2) with head-to-tail orientation (Bet v 1→Mal d 1) via dipeptide linker EF, is particularly preferred.

The hybrid variant according to the present invention shows an IgE-binding reduction by at least 10%, preferably 50%, and more preferably 70% compared to the wt hybrid.

Figure 9:
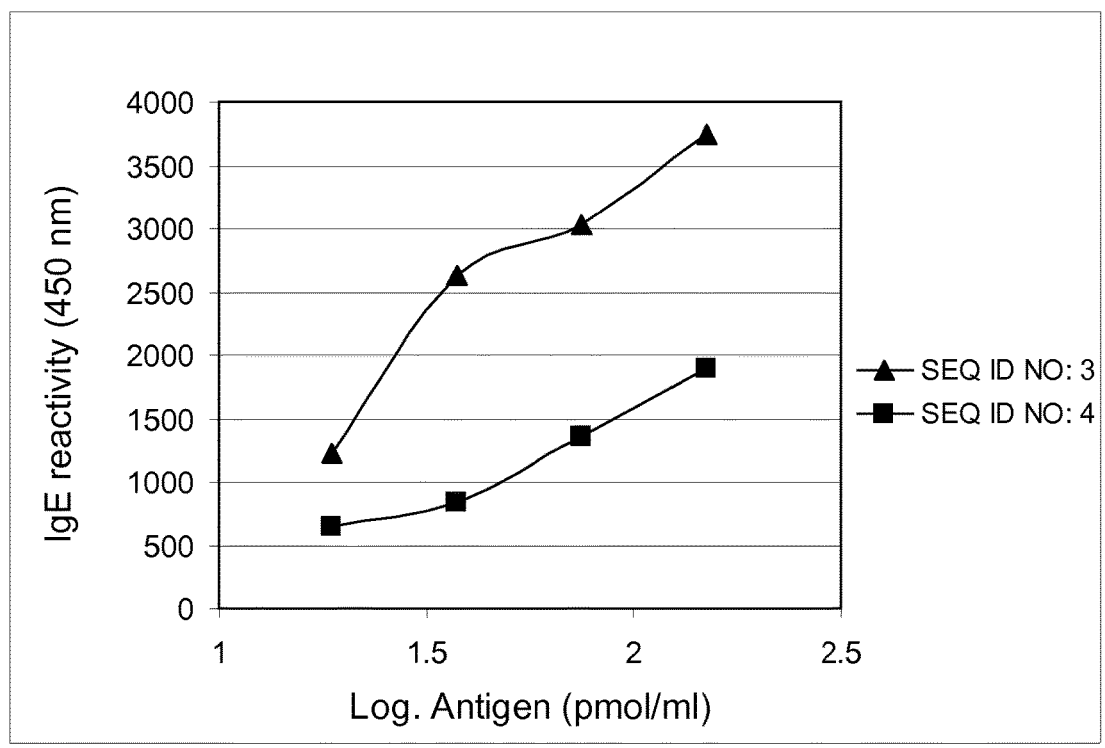
FIG. 9 shows the IgE reactivity of variant SEQ ID NO: 4.

The IgE reactivity of variant SEQ ID NO: 4 was analysed in a sera pool from individuals allergic to birch pollen and apple by ELISA assay (FIG. 9). When incubated with the sera, said variant exhibited a mean reduction of 55.1% in IgE reactivity compared with the wt hybrid (SEQ ID NO: 3).

These results were confirmed by ELISA-inhibition experiments. It has been observed that at equal concentrations (1.25 µg/ml) of inhibitor, binding between allergen wt Bet v 1 (SEQ ID NO: 5) adsorbed on wells and the specific IgE contained in the sera of 7 patients is inhibited by an average of 79.9% when the serum is pre-treated with a mixture of the single wt allergens, 53.3% when pre-incubated with a mixture of the two mutagenised components, 63.3% when pre-treated with SEQ ID NO: 3, and 32.1% when the serum is pre-incubated with SEQ ID NO: 4 (Table 2 and FIG. 10A). The ability of mutant hybrid SEQ ID NO: 4 to compete in Bet v 1-IgE binding diminishes significantly ($p<0.05$) compared with both SEQ ID NO: 3 and the mixture of the two mutagenised allergens (mut Bet v 1—SEQ ID NO:6 and mut Mal d 1—SEQ ID NO:2).

Figure 10:
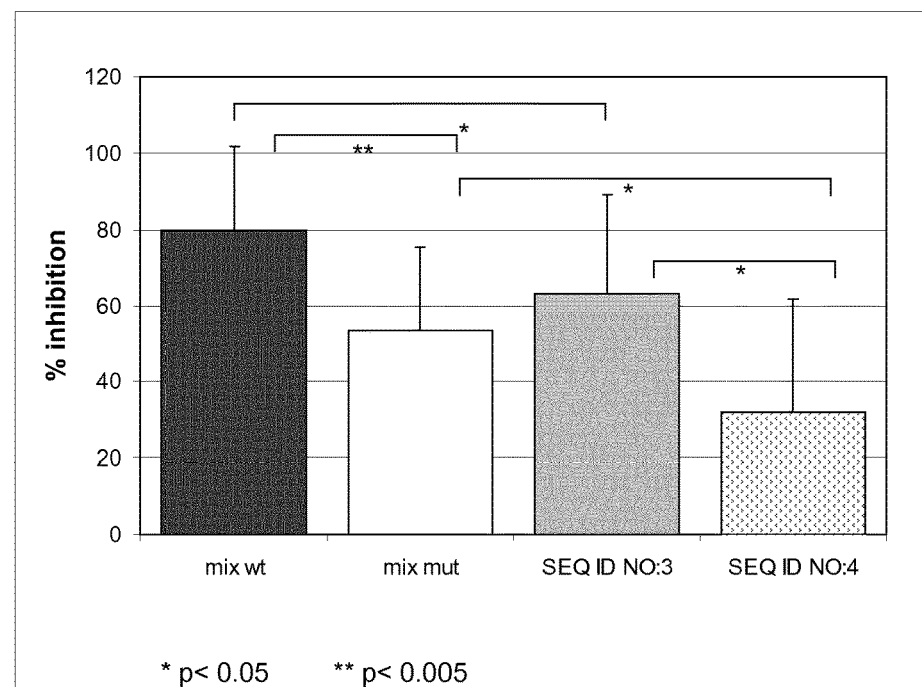
FIG. 10A shows results of Elisa-inhibition experiments of bending between wt Bet v 1 allergen and specific IgE.
FIG. 10B shows results of Elisa-inhibition experiments of binding between wt Mal d 1 allergen and specific IgE.
Figure 10:
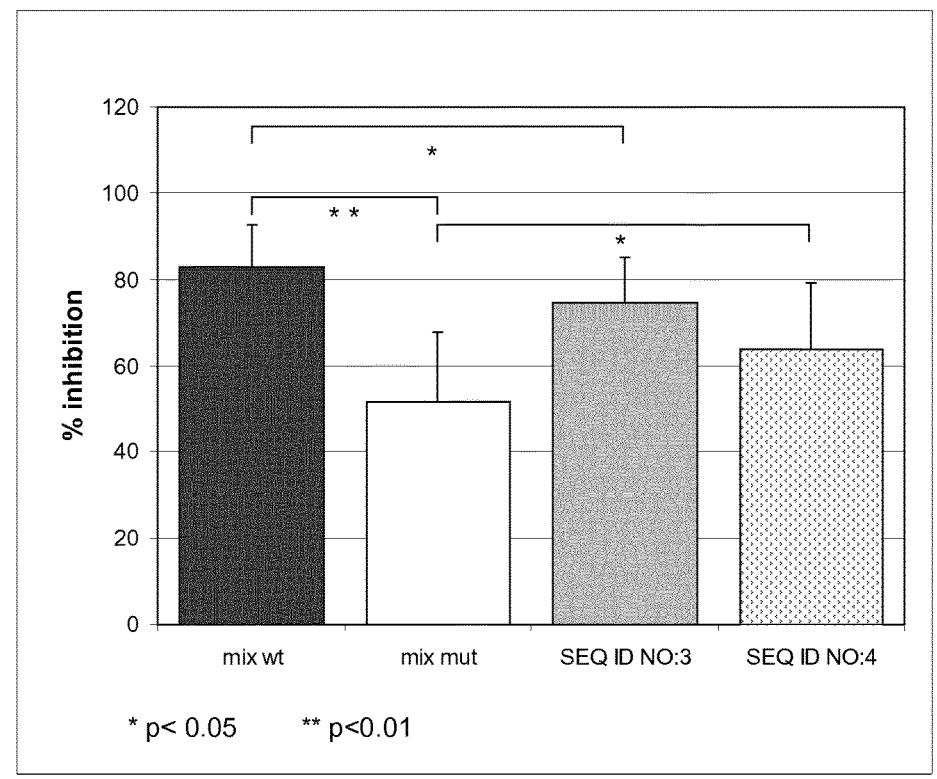

At the same quantity (1.25 µg/ml) of inhibitor, binding between wt Mal d 1 allergen (SEQ ID NO:1) adsorbed on wells and the specific IgE contained in the sera of the 7 patients is inhibited by an average of 82.8% when the serum is pre-treated with a mixture of the single wt allergens, 51.6% when pre-incubated with a mixture of the two mutagenised components, 74.6% when pre-treated with SEQ ID NO: 3, and 63.6% when the serum is pre-incubated with SEQ ID NO: 4 (Table 3 and FIG. 10B). The results obtained for Mal d 1 are comparable with those measured for Bet v 1, with the exception of SEQ ID NO:4, which proved more reactive against Mal d 1.

Figure 11:
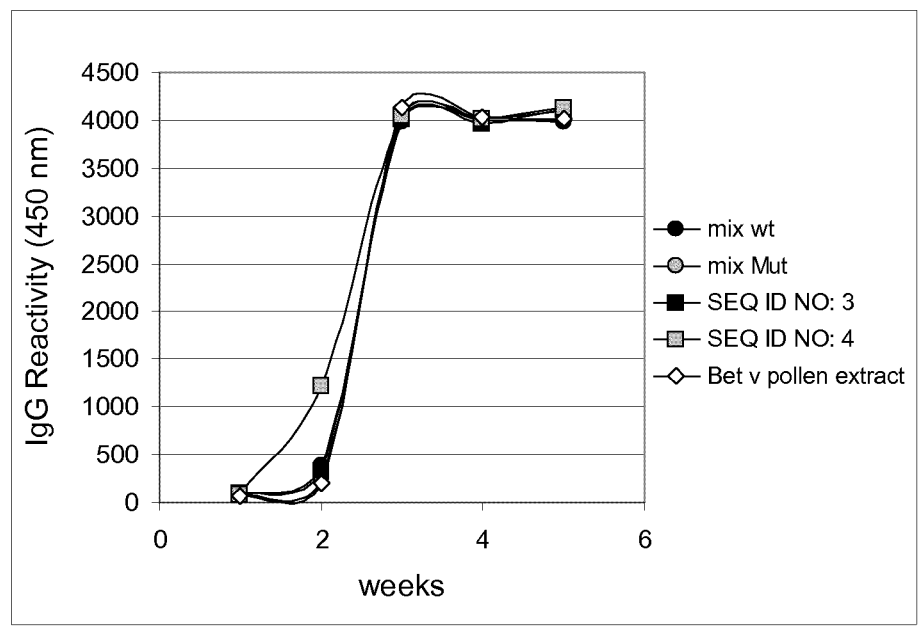
FIG. 11 shows production of specific IgGs able to recognize Bet v 1 allergen.

It was also observed that the hypoallergenic variant SEQ ID NO:4, used to immunise Balb/c mice, induces the production of specific IgGs able to recognise Bet v 1 allergen present in *Betula verrucosa* extract (FIG. 11). The hybrid molecule SEQ ID NO:4 induces a specific IgG response similar to that induced in mice by birch extract, by SEQ ID NO: 3, or by a mixture of the respective wt or mutagenised allergens. Conversely, the antibodies present in the sera of animals immunised with an unrelated antigen are unable to recognise SEQ ID NOs: 3 and 4 and mixtures of the wt and mutant allergens.

Figure 12:
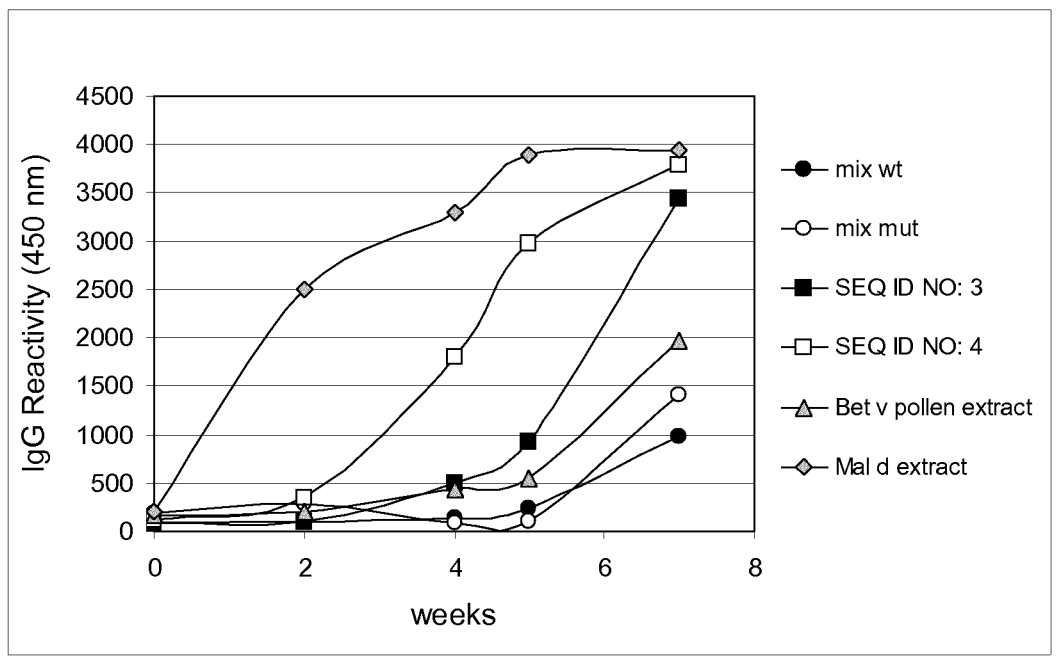
FIG. 12 shows specific IgG response induced by the hypoallergenic hybrid variant SEQ ID NO: 4 to the components of *Malus domestica* pulp extract.

The hypoallergenic hybrid variant SEQ ID NO: 4 is also able to induce a specific IgG response to the components of *Malus domestica* pulp extract (FIG. 12). Five weeks after the first immunisation, the IgG response induced by immunising with SEQ ID NO: 4 is 30 times greater than that obtained by immunising with equimolar quantities of a mixture of the two single mutagenised variants (mut mix), and 3.2 times greater than the wt hybrid allergen SEQ ID NO: J. Immunisation with birch extract induces the production of IgGs able to recognise the Mal d 1 contained in apple extract as from the fifth week.

Figure 13:
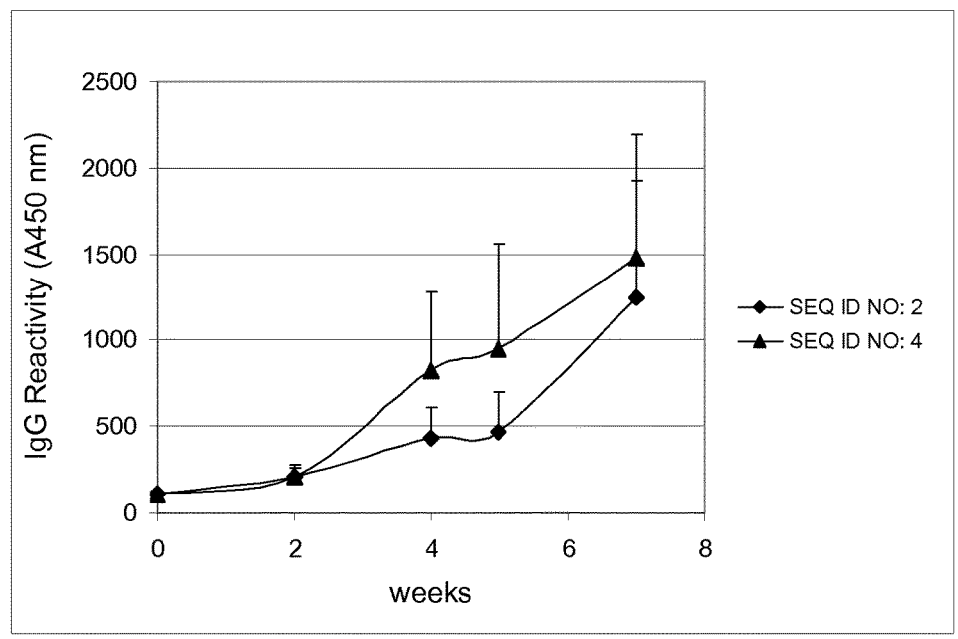
FIGS. 13-A, B show the induction of IgG antibodies specific for wt Mal d 1 and mutant Mal d 1, respectively, in mice immunized with SEQ ID NO: 2 and SEQ ID NO: 4.
Figure 13:
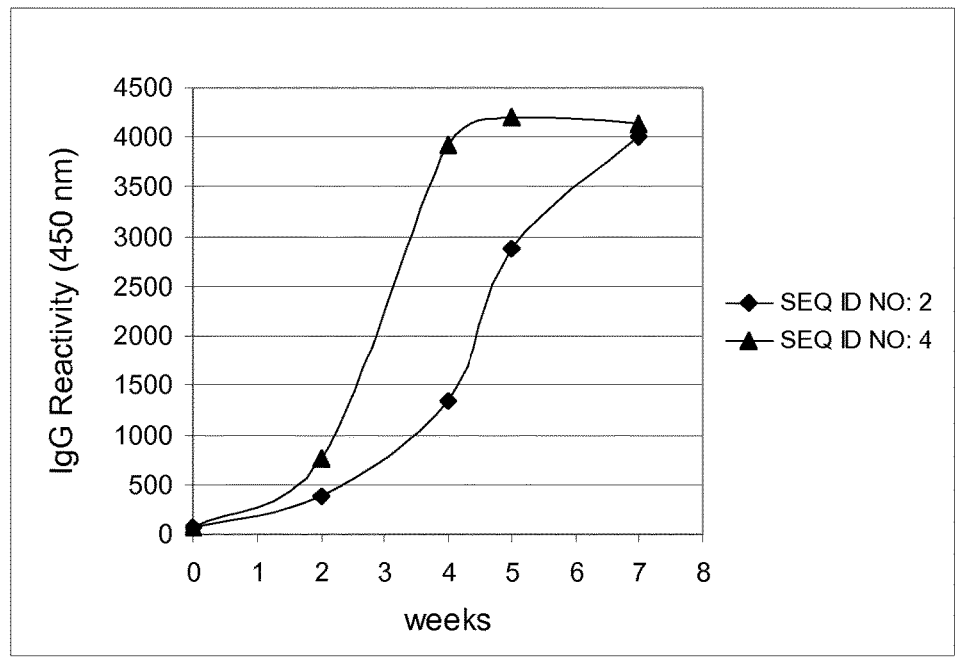

Moreover, the immunogenicity of hypoallergenic variant SEQ ID NO: 2 increases when it is part of the hybrid hypoallergenic molecule SEQ ID NO: 4. The induction of IgG antibodies specific for wt Mal d 1 (SEQ ID NO: 1) and mutant Mal d 1 (SEQ ID NO: 2) is much higher and earlier in mice immunised with hybrid variant SEQ ID NO: 4 than in mice immunised with the single allergen SEQ ID NO: 2. A substantial increase in induction with SEQ ID NO: 4 is already observed in the fourth week of treatment, whereas it takes at least seven weeks to obtain the same response by immunising the animals with protein SEQ ID NO: 2 (FIG. 13-A,B).

Figure 14:
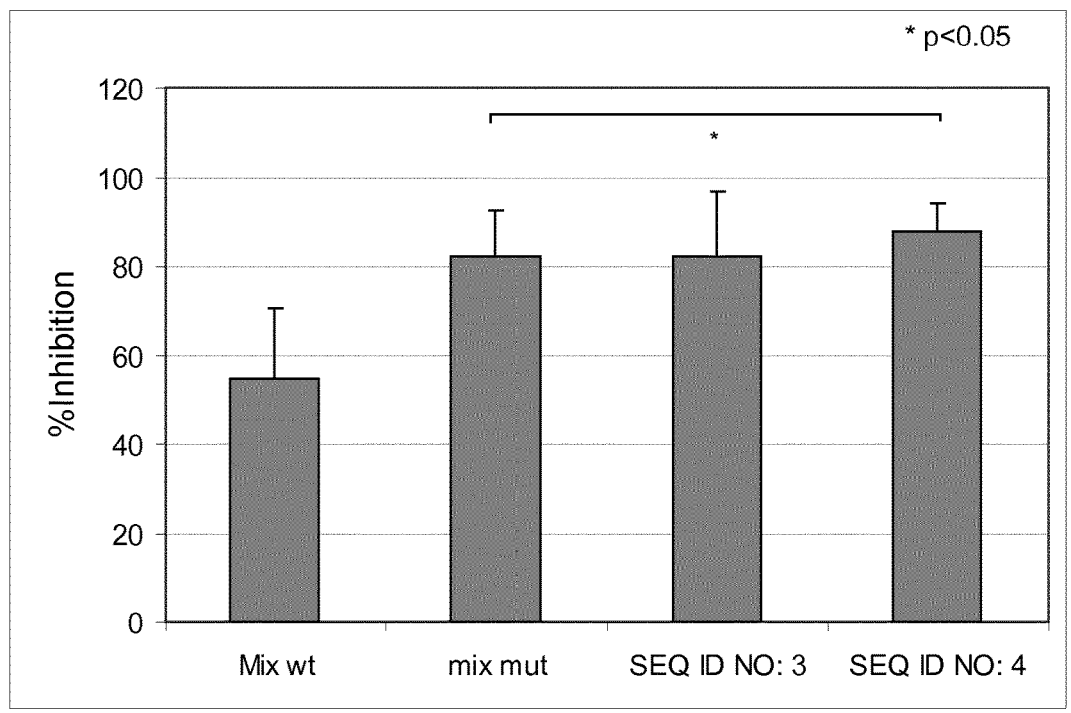
FIG. 14 shows IgG antibodies produced against SEQ ID NO: 4 inhibiting the biding between Bet V 1 to IgEs of patients allergic to birch and apple

As regards the induction of protective antibodies able to inhibit binding between allergen and IgEs, it has been observed that the IgG antibodies produced against SEQ ID NO: 4 inhibit the binding of Bet v 1 (SEQ ID NO: 5) to IgEs of patients allergic to birch and apple more effectively than those induced by the mixture of the two single mutated variants (mut mix) (p<0.05) (FIG. 14). ELISA inhibition experiments have demonstrated that the IgGs produced in mice immunised with SEQ ID NO: 4 inhibits the IgE reactivity of seven sera of patients by an average of 87.7% (with values ranging from 77.4 to 94.7%) and those produced against a mixture of the two mutagenised variants (mut mix) by 82% (63.5-92.3%); the IgG antibodies produced against the mixture of wt proteins (wt mix) inhibit binding by an average of 54.7% (32.4-68.6%), and those obtained by immunising with wt hybrid SEQ ID NO: 3 by 82.2% (51.9-93.5%).

Figure 15:
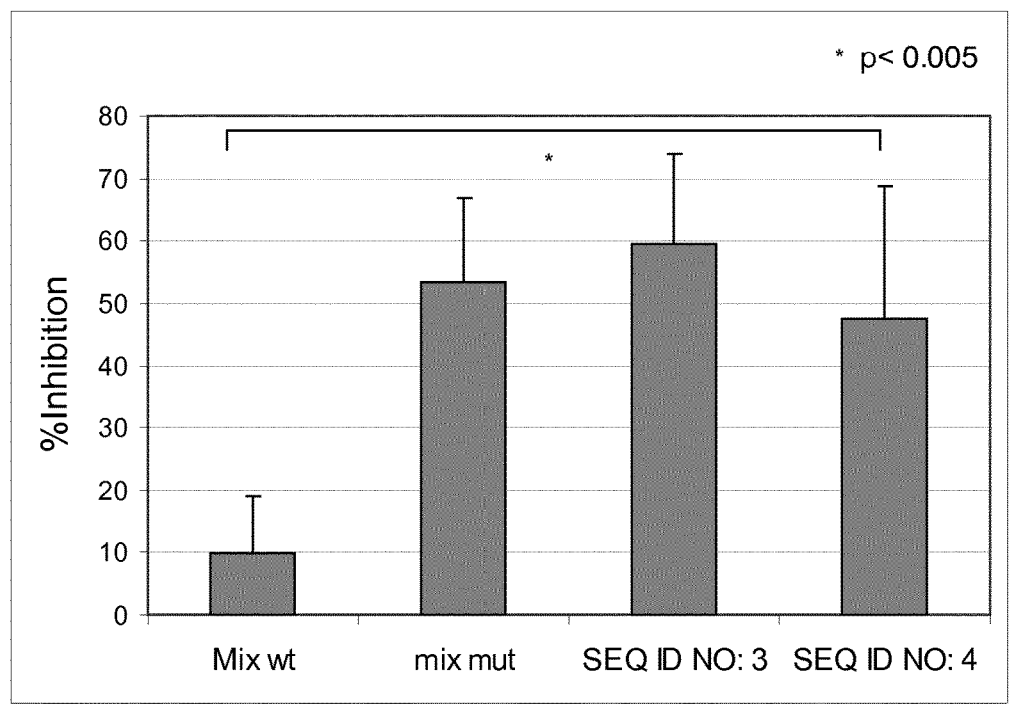
FIG. 15 shows IgG antibodies induced in mice immunized with SEQ ID NO: 4 inhibiting the binding between Mal d 1 and IgEs from the sera of patients allergic to birch and apple.

The IgG antibodies induced in mice immunised with SEQ ID NO: 4 also inhibit binding between Mal d 1 (SEQ ID NO: 1) and the IgEs from the sera of patients allergic to birch and apple by an average of 47.5%, 9.9% if they are immunised with a mixture of wt proteins, 53.5% with a mixture of mutated variants, and 59.4% with immunogen SEQ ID NO: 3 (FIG. 15).

The serum of the non-immunised animals used as control does not cause any inhibition of specific IgE binding to Bet v 1 and Mal d 1.

The substitution variants according to the invention can easily be prepared by mutagenesis of the cDNA sequence of Mal d 1 (SEQ ID NO: 7), Bet v 1 (SEQ ID NO: 8), their isoforms or natural variants, or of the cDNA sequence of the wt hybrid (SEQ ID NO: 9), using techniques known to the skilled person (21).

SEQ ID NOs: 10 and 19 report the cDNA sequences encoding for the (monomeric) double-substitution variant or the hybrid variant identified as SEQ ID NOs: 2 and 4 respectively.

Further aspects of the invention therefore relate to a nucleic acid molecule encoding for a variant of allergen Mal d 1 described herein, for a peptide deriving from it or for the hybrid protein Mal d 1-Bet v 1, and an expression vector containing said molecule together with elements for expression control in eukaryotic or prokaryotic cells, such as transcription promoters or enhancers, signal sequences or other transcription regulation sequences. The vector can be a plasmid, virus, phage or any other vector commonly used in genetic engineering.

The invention also includes a prokaryotic or eukaryotic host cell transformed or transfected with the vector according to the invention. Prokaryotic cells such as *Escherichia coli* and *Bacillus subtilis*, or eukaryotic cells such as *Saccharomyces cerevisiae*, are generally used for vector cloning and cDNA expression.

The hypoallergenic variants according to the invention can also be produced as fusion proteins.

In view of their reduced IgE reactivity, the Mal d 1 variants according to the present invention could conveniently be employed to prepare pharmaceutical compositions (e.g. tablets) for use in immunotherapy of patients allergic to apple and/or *Betula verrucosa* pollen.

A further aspect of the invention therefore relates to a pharmaceutical composition containing an effective quantity of hypoallergenic variant of Mal d 1, optionally in combination with other *Betula verrucosa* allergens, together with pharmaceutically acceptable carriers, excipients or adjuvants. In a preferred embodiment, said pharmaceutical composition is in the form of a suitable vaccine for preventive or therapeutic treatment of allergic diseases, such as bronchial asthma and rhinitis, conjunctivitis and oral allergy syndrome. The sublingual, subcutaneous and transdermal administration forms are most preferred.

The vaccination principles and methods are known to the skilled person and described, for example, in (22).

The examples below illustrate the invention in greater detail.

EXAMPLES

Unless otherwise indicated, the methods used in the following examples are described in Sambrook, Fritsch E T Maniatis "Molecular Cloning: A Laboratory Manual" II Ed. Vol. 1-2-3 CSH Lab Press 1989.

Example 1—Site-Specific Mutagenesis of the cDNA Coding for Mal d 1 Allergen

Site-specific mutagenesis of the cDNA coding for Mal d 1 allergen (SEQ ID NO: 7, preceded at 5' by a sequence coding six histidines) was carried out by cDNA cloning in a prokaryotic vector (pBluescript, GenBank acc. n. X52327) followed by PCR amplification. The oligonucleotides used as primers in the PCR reaction (Table 1) carried the appropriate base substitutions. For each mutagenesis, a complementary oligonucleotide binding to a corresponding region of the DNA strand was used (21). After amplification, the unaltered original template was selectively degraded with enzymatic digestion catalyzed by the restriction enzyme Dpn I. *Escherichia coli* cells were then transformed with the mutagenized molecules. Clones obtained from single bacterial colonies were sequenced according to Sanger to determine the correct base modification and the absence of non-specific mutations in the cDNA.

TABLE 1

Sequences of the oligonucleotides used as primers in site-specific mutagenesis. The mutated bases are in bold character.

| Oligo-nucleotide | Sequence |
|---|---|
| Mald1D25 | Gcc ttt gtc ctt gct gct gac aac ctc (SEQ ID NO: 12) |
| Mald1N78 | Gtt gac gag gca gcc tac tca tac gcc (SEQ ID NO: 13) |

Example 2—Construction of a Plasmid Coding for Wild-Type Bet v 1-Mal d 1 Hybrid Molecule (wtHybrid)

The hybrid molecule containing the genetic information for wild-type Bet v 1-Mal d 1 hybrid was obtained by fusion of cDNAs coding for the single allergens.

The cDNAs encoding mature Bet v 1 and Mal d 1 proteins were obtained separately by PCR using Bet v 1 DIM FW (ggt gtt ttc aat tac gaa act g—SEQ ID NO:14) and Bet v 1 DIM Eco RV (Gc gaattc gtt gta ggc atc gga g—SEQ ID NO:15) oligonucleotide primers for Bet v 1 and Mal d 1 DIM Eco FW (cgc gaattc ggt gtc tac aca ttt gag aac g—SEQ ID NO:16) and Mal d 1 DIM Bam RV (Gcg ggatcc tta gtt gta tgc gtc ggg gtg—SEQ ID NO:17) oligonucleotide primers for Mal d 1. Bet v 1 SEQ ID NO: 8 and Mal d 1 SEQ ID NO: 7 clones were used as templates.

The amplification product obtained from Bet v 1 was re-amplified by replacing Bet v 1 DIM FW primer with Bet v 1 DIM Kpn FW (gcg ggtacccatatg cat cac cat cac cat cac ggt gtt ttc aat tac gaa act g—SEQ ID NO:18), whereby a sequence coding for six histidines upstream of Bet v 1 sequence was inserted. A Kpn I site and a Nde I site (containing the ATG) were inserted at 5' of Bet v 1 amplification product, and a Eco R I site was inserted at its 3' in place of the stop codon. An Eco R I site was inserted in place of the ATG at 5' of Mal d 1, and a Bam H I site was inserted at its 3' after the stop codon. The amplified products were purified, digested with Kpn I and Eco R I restriction enzymes (Bet v 1), or Eco R I and Bam H I (Mal d 1) (restriction sites are underlined in the primers), and subsequently inserted into Kpn I/Bam H I sites of pEt 3c vector (Stratagene, La Jolla, Calif.) to obtain a construct capable of expressing a Bet v 1-Mal d 1 fusion protein preceded by a sequence of six histidines. Introduction of Eco R I restriction site, that is necessary for cloning of fragments, allowed for insertion of two amino acids (glutamic acid and phenylalanine) at the junction of the two proteins without altering the reading frame (FIG. 8).

Clones obtained from single bacterial colonies were sequenced by the Sanger method to verify that base change was correct, and the absence of unspecific mutations in the cDNA.

Example 3—Construction of a Plasmid Coding for Mutant Bet v 1-Mal d 1 Hybrid Molecule (MutHybrid)

The hybrid molecule coding for mutant Bet v 1-Mal d 1 hybrid was obtained following the method described in EXAMPLE 2 for the wild-type hybrid variant.

The oligonucleotide pairs used in the PCR reaction were identical, while the cDNAs used as templates encoded for two hypoallergenic variants whose sequences are herein identified as SEQ ID NO: 20 (for Bet v 1 mutant) and SEQ ID NO: 10 (Mal d 1 mutant).

Clones obtained from single bacterial colonies were sequenced by the Sanger method to verify that base change was correct, and the absence of unspecific mutations in the cDNA.

Example 4—Production of Mal d 1 and Bet v 1 Proteins, Respective Mutants, wtHybrid and MutHybrid Wild-type Bet v 1 (SEQ ID NO:8) and Mal d 1 (SEQ ID NO:7) cDNAs, mutagenized cDNAs (SEQ ID NO:20 and SEQ ID NO:10), and engineered wt and Mut Hybrid cDNAs (SEQ ID NO: 9 e 19), preceded by the sequence coding for six histidines, were cloned in an expression vector and expressed in *Escherichia coli* cells according to standard protocols (23). Cells were collected by centrifugation and resuspended in 100 mM $NaH_2PO_4$ buffer, pH 8 and lysed by sonication. The recombinant proteins were separated by centrifugation. The pellet containing an insoluble protein aggregate was resuspended in denaturing buffer urea 6 M, $NaH_2PO_4$ 100 mM, Tris 10 mM pH 8 and stirred for 60 min at 20° C. The solubilized recombinant proteins were separated from insoluble debris by centrifugation and purified from the supernatant by affinity chromatography using agarose columns to which nitrilotriacetic acid chelating nickel ions that interact with the six-histidine portion fused to allergen was bound. Purified proteins were refolded by dialysis for 18 hours at 4° C. in a $(NH_4)HCO_3$ 5 mM solution.

Example 5—Characteristics of Sera from Allergic Subjects

Sera were collected from subjects with a clinical history of seasonal allergy to *Betula verrucosa* pollen, and 3+ reactivity specific for Bet v 1 and Mal d 1 allergens and used in single or pooled form. A pool of sera from non-allergic subjects was used as a negative control.

Example 6—ELISA Analysis of Mal d 1 Variants Reactivity to IgEs from a Serum Pool Serially three-fold diluted aliquots in 50 mM carbonate/bicarbonate buffer, pH 9.6 of wt allergen (SEQ ID NO: 1) and mutagenized variants (SEQ ID NO:2, SEQ ID NO:11) were adsorbed on wells of polystirene plates for ELISA assay by incubation at 4° C. for 16 hours. The wells were washed with washing solution (60 mM phosphate buffer, pH 6.5, containing 0.05% Tween-20), and blocked with diluting solution (25% goat serum, 1 mM EDTA, 0.05% Tween 20, 0.01% Thiomersal in 150 mM phosphate buffer, pH 7.4). 60 μl aliquots in dilution buffer of a pool of human sera from RAST 3+ or non-allergic subjects were added to each sample and incubated at 25° C. for 2 hours. After three washes, peroxidase-conjugated anti human-IgE serum (1:4000 in diluting buffer) was added, followed by incubation at 25° C. for 1.5 hours. After three washes, the colorimetric reaction was developed by adding 100 μl of TMB reagent (BioFX Laboratories, Owings Mills, Md.) and incubating for 15 minutes at 25° C. The reaction was stopped by adding 100 μl of 1 N HCl and read at 450 nm using a microplate reader spectrophotometer. Results were confirmed by three independent experiments. The same protocol was applied with some modifications to test IgE reactivity of the engineered wt and Mut hybrids.

Serial dilution of the hybrid allergens (SEQ ID NO:3 and 4) were prepared in a 1:2 ratio in 50 mM carbonate/bicarbonate buffer, pH 9.6, starting from 150 nM and adsorbed on wells of polystirene plates. A pool of sera positive to Bet v 1 and Mal d 1 or from non-allergic subjects as negative control were diluted 1:2.5 in diluting solution, added (70 μl) to each well and incubated at 25° C. for 3 hours.

Example 7—ELISA Inhibition Assay—Monomeric Variants of Mal d 1 Inhibit Binding of Mal d 1 to IgEs in Serum Equal amounts (0.1 μg) of wild type Mal d 1 in 50 mM carbonate/bicarbonate buffer, pH 9.6, were adsorbed onto wells of polystyrene plates for ELISA assay by incubating at 4° C. for 16 hours. Wells were then washed with washing solution (60 mM phosphate buffer, pH 6.5, containing 0.05% Tween-20), and free sites were blocked with diluting solution (15% goat serum, 1 mM EDTA, 0.05% Tween-20, in 150 mM phosphate buffer, pH 7.4). Aliquots (100 µl) of a 1:3 dilution of pooled human sera positive to Bet v 1 and Mal d 1 were pre-incubated with four-fold serial dilutions of wt or mutagenized allergens starting from 5 µg/ml at 25° C. for 2 hours. The mixes were then added to each well, and incubated at 4° C. for 16 hours. After three washes with 0.06 M phosphate, pH 6.5, 0.05% Tween-20 buffer, anti-human IgE peroxidase-conjugated serum diluted 1:4000 in diluting buffer was added, and incubated at 25° C. for 1.5 hours. After three washes, colorimetric reaction development was obtained by adding 100 µl TMB reagent (BioFX Laboratories, Owings Mills, Md.), and incubating for 15 minutes at 25° C. The reaction was stopped by adding 100 µl N HCl, and evaluated by reading at 450 nm with a spectrophotometer. Inhibition percentage was calculated by using the following formula: 100×[(A−B)/A], where A is absorbance at 450 nm in the absence of inhibitor, and B is absorbance in the presence of inhibitor. Data are representative of three independent experiments.

Example 8—ELISA Inhibition Assay—Monomeric Variants of Mal d 1 Inhibit Binding of Bet v 1 to IgEs in Serum Equal amounts (0.1 µg) of wild type Bet v 1, in 50 mM carbonate/bicarbonate buffer, pH 9.6, were adsorbed onto wells of polystyrene plates for ELISA assay by incubating at 4° C. for 16 hours. Wells were then washed with washing solution (60 mM phosphate buffer, pH 6.5, containing 0.05% Tween-20), and free sites were blocked with diluting solution (15% goat serum, 1 mM EDTA, 0.05% Tween-20, in 150 mM phosphate buffer, pH 7.4). Aliquots (100 µl) of a 1:3 dilution of pooled human sera positive to Bet v 1 and Mal d 1 were pre-incubated with serial four-fold dilutions of wt Bet v 1, wt Mal d 1 or mutagenized variants starting from 10 µg/ml at 25° C. for 2 hours. The mixes were then added to each well, and incubated at 4° C. for 16 hours. After three washes with 0.06 M phosphate, pH 6.5, 0.05% Tween-20 buffer, anti-human IgE peroxidase-conjugated serum diluted 1:4000 in diluting buffer was added, and incubated at 25° C. for 1.5 hours. After three washes, colorimetric reaction development was obtained by adding 100 µl TMB reagent (BioFX Laboratories, Owings Mills, Md.), and incubating for 15 minutes at 25° C. The reaction was stopped by adding 100 µl 1 N HCl, and evaluated by reading at 450 nm with a spectrophotometer. Inhibition percentage was calculated by using the following formula: 100×[(A−B)/A], where A is absorbance at 450 nm in the absence of inhibitor, and B is absorbance in the presence of inhibitor. Values were confirmed by three independent experiments.

Example 9—ELISA Inhibition Assay—SEQ ID NO: 3 and SEQ ID NO: 4 Inhibit Binding of Bet v 1 or Mal d 1 to IgEs in Serum Equal amounts (0.1 µg) of wild type Bet v 1 or Mal d 1, in 50 mM carbonate/bicarbonate buffer, pH 9.6, were adsorbed onto wells of polystyrene plates for ELISA assay by incubating at 4° C. for 16 hours. Wells were then washed with washing solution (60 mM phosphate buffer, pH 6.5, containing 0.05% Tween-20), and free sites were blocked with diluting solution (15% goat serum, 1 mM EDTA, 0.05% Tween-20, in 150 mM phosphate buffer, pH 7.4). Aliquots (70 µl) of a 1:3 dilution of a pool of human sera positive to Bet v 1 and Mal d 1 were pre-incubated with equal amounts (1.25 µg/ml) of wild type allergen, mutagenized or engineered variants (hybrids) at 25° C. for 2 hours. The mixes were then added to each well, and incubated at 4° C. for 16 hours. After three washes with 0.06 M phosphate, pH 6.5, 0.05% Tween-20 buffer, anti-human IgE peroxidase-conjugated serum diluted 1:4000 in diluting buffer was added, and incubated at 25° C. for 1.5 hours. After three washes, colorimetric reaction development was obtained by adding 100 µl TMB reagent (BioFX Laboratories, Owings Mills, Md.), and incubating for 15 minutes at 25° C. The reaction was stopped by adding 100 µl 1 N HCl, and evaluated by reading at 450 nm with a spectrophotometer. Inhibition percentage was calculated by using the following formula: 100×[(A−B)/A], where A is absorbance at 450 nm in the absence of inhibitor, and B is absorbance in the presence of inhibitor.

TABLE 2

Hybrid wild-type- and mutagenized-molecules inhibit Bet v 1-IgE binding

| Serum | wt Mix | Mut Mix | SEQ ID NO: 3 | SEQ ID NO: 4 |
|---|---|---|---|---|
| 1 | 97.1 | 88.4 | 93.6 | 90.2 |
| 2 | 96.6 | 72.8 | 85.1 | 36.4 |
| 3 | 90.9 | 52.3 | 76.2 | 35.9 |
| 4 | 81.2 | 56.5 | 61.7 | 35.9 |
| 5 | 91.6 | 41.0 | 50.8 | 7.8 |
| 6 | 65.2 | 41.8 | 56.6 | 0 |
| 7 | 36.8 | 20.6 | 15.9 | 18.2 |
| Mean % inhibition | 79.9 | 53.3 | 63.3 | 32.1 |
| Standard deviation | 22.02 | 22.2 | 25.77 | 29.53 |

TABLE 3

Hybrid wild-type- and mutagenized-molecules inhibit Mal d 1-IgE binding

| serum | wt Mix | Mut Mix | SEQ ID NO: 3 | SEQ ID NO: 4 |
|---|---|---|---|---|
| 1 | 95.5 | 76.7 | 92.0 | 91.0 |
| 2 | 93.9 | 42.4 | 84.5 | 41.9 |
| 3 | 80.5 | 49.0 | 75.1 | 66.3 |
| 4 | 77.3 | 46.0 | 71.3 | 64.3 |
| 5 | 88.3 | 27.6 | 68.0 | 50.8 |
| 6 | 73.7 | 53.9 | 70.5 | 70.8 |
| 7 | 70.3 | 65.6 | 60.6 | 60.4 |
| Mean % inhibition | 82.8 | 51.6 | 74.6 | 63.6 |
| Standard deviation | 9.9 | 16.0 | 10.6 | 15.6 |

Example 10—Immunization of Balb/c Mice

Ten groups of mice each composed of five Balb/c strain female animals (Charles River) were subcutaneously immunized with 150 pmol of wt, mutagenized or engineered (hybrid) allergen or 10 µg of extract of *Betula verrucosa* pollen or *Malus domestica* mixed with 2 mg of Al(OH)$_3$) in 200 µl saline. Other two boosts were performed after 21 and 42 days. As a control, five mice received the same treatment with an unrelated antigen (data not shown). Two, four, five and seven weeks following first immunization, blood collection was performed from jugular vein of mice, and antibody response to the respective immunogen was checked by ELISA. In mice immunized with SEQ ID NO: 2 and 4, the capability to recognize the wild-type protein or extracts of *Betula verrucosa* pollen and *Malus domestica* was also analyzed. Sera from mice were pooled based on immunogenic type and time elapsed from first immunization.

Example 11—Analysis of Specific IgG Response in Immunized Mice by ELISA Assay

Equal amounts of extract of *Betula verrucosa* pollen and *Malus domestica* (20 µg/ml) or wt Bet v 1 or Mal d 1 or SEQ ID NO: 2 (2 µg/ml), in 50 mM carbonate/bicarbonate buffer, pH 9.6, were adsorbed onto wells of polystyrene plates for ELISA assay by incubating at 4° C. for 16 hours. Wells were then washed with washing solution (60 mM phosphate buffer, pH 6.5, containing 0.05% Tween-20), and free sites were blocked with diluting solution (15% goat serum, 1 mM EDTA, 0.05% Tween-20, in 150 mM phosphate buffer, pH 7.4). Equal aliquots (100 µl) of each mouse serum or pooled sera were added to each well at a 1:1000 dilution in diluting buffer, and incubated at 25° C. for 2 hours. After three washes, anti-total mouse IgG peroxidase-conjugated serum diluted 1:2000 in diluting buffer was added and incubated at 25° C. for 1.5 hours. After three washes, colorimetric reaction development was obtained by adding 100 µl TMB reagent (BioFX Laboratories, Owings Mills, Md.), and incubating for 20 minutes at 25° C. The reaction was stopped by adding 100 µl 1 N HCl and read at 450 nm with a spectrophotometer. Data show the mean reactivity obtained by analysis of the sera from 5 mice for each group.

Example 12—ELISA Inhibition Assay. IgGs Against SEQ ID NO: 2 and SEQ ID NO: 4 Inhibit the Binding Between Wild Type Bet v 1 or Mal d 1 and IgEs in the Sera of Allergic Patients Positive to Bet v 1 and Mal d 1

Equal amounts of Bet v 1 (0.1 µg) or Mal d 1 (0.2 µg) in 50 mM carbonate/bicarbonate buffer, pH 9.6, were adsorbed onto wells of polystyrene plates for ELISA assay by incubating at 4° C. for 16 hours. Wells were then washed with washing solution (60 mM phosphate buffer, pH 6.5, containing 0.05% Tween-20), and free sites were blocked with diluting solution (15% goat serum, 1 mM EDTA, 0.05% Tween-20, in 150 mM phosphate buffer, pH 7.4). Aliquots (100 µl) of 1:10 diluted pools from mouse sera collected after seven weeks from first immunization were incubated at 4° C. for 16 hours. After three washes with 0.06 M phosphate buffer, pH 6.5, 0.05% Tween-20, seven 1:3 diluted human sera positive to Bet v 1 and Mal d 1 were added at 25° C. for 3 hours. After three washes with 0.06 M phosphate buffer, pH 6.5, 0.05% Tween-20, anti-human IgE peroxidase-conjugated serum diluted 1:4000 in diluting buffer was added, and incubated at 25° C. for 1.5 hours. After three washes, colorimetric reaction development was obtained by adding 100 µl TMB reagent (BioFX Laboratories, Owings Mills, Md.), and incubating for 20 minutes at 25° C. The reaction was stopped by adding 100 µl 1 N HCl and read at 450 nm with a spectrophotometer. Inhibition percentage was calculated by using the following formula: $100 \times [(A-B)/A]$, where A is absorbance at 450 nm in the absence of inhibiting human serum, and B is absorbance in the presence of inhibiting human serum.

Example 13—Statistical Analysis

In the figures, results are expressed as mean values plus corresponding standard deviations.

UNISTAT 5.5 Light for Excel software was used for statistical analyses. Data were analyzed by paired t-Test.

REFERENCES

1) Batard T., Didierlaurent A., Chabre H., et al., (2005). "Characterization of wild-type recombinant Bet v 1a as a candidate vaccine against birch pollen allergy". Int Arch Allergy Immunol. 136: 239-249.
2) Vieths S., Scheurer S., Ballmer-Weber B. (2002). "Current understanding of cross-reactivity of food allergen and pollen". Ann N Y Acad Sci, 964:47-68.
3) Malling H. J., (1998) "Immunotherapy as an effective tool in allergy treatment". Allergy, 53: 461.
4) Ballmer-Weber B K, Wuthrich B, Wangorsch A, Fotisch K, Altmann F, Vieths S. (2001) "Carrot allergy: double-blinded, placebo-controlled food challenge and identification of allergens". J Allergy Clin Immunol 108: 301-307.
5) Asero R. (1998). "Effects of birch pollen-specific immunotherapy on apple allergy in birch pollen-hypersensitive patients". Clin Exp Allergy; 28(11):1368-73.
6) Bolhaar S T, Tiemessen M M, Zuidmeer L, van Leeuwen A, Hoffmann-Sommergruber K, Bruijnzeel-Koomen C A, Taams L S, Knol E F, van Hoffen E, van Ree R, Knulst A C. (2004). "Efficacy of birch-pollen immunotherapy on cross-reactive food allergy confirmed by skin tests and double-blind food challenges". Clin Exp Allergy. 34(5): 761-9.
7) Hansen K S, Khinchi M S, Skov P S, Bindslev-Jensen C, Poulsen L K, Malling H J (2004) "Food allergy to apple and specific immunotherapy with birch pollen". Mol Nutr Food Res. 48(6):441-8.
8) Klinglmayr E, Hauser M., Zimmermann F, Dissertori O., Lackner P, Wopfner N., Ferreira F S., Wallner M. (2009). "Identification of B-cell epitopes of Bet v 1 involved in cross-reactivity with food allergens". Allergy; 64:647-651.
9) Bolhaar STHP, Zuidmeer L, Ma Y, Ferreira F, Bruijnzeel-Koomen CAFM, Hoffmann-Sommergruber K, van Ree R, Knulst A C. (2005). "A mutant of the major apple allergen, Mal d 1, demonstrating hypo-allergenicity in the target organ by double-blind placebo-controlled food challenge". Clin Exp Allergy 35:1638-1644.
10) Vanek-Krebitz M., Hoffmann-Sommergruber K., Laimer da Camara Machado M., Susani M., Ebner C., Kraft D., Scheiner O., Breiteneder H. (1995). "Cloning and sequencing of Mal d 1, the major allergen from apple (*Malus domestica*), and its immunological relationship to Bet v 1, the major birch pollen allergen". BBRC 214 (2):538-551.
11) Gao Z, van de Weg E W, Matos C I, Arens P, Bolhaar S T, Knulst A C, Li Y, Hoffmann-Sommergruber K, Gilissen L J. "Assessment of allelic diversity in intron-containing Mal d 1 genes and their association to apple allergenicity". (2008). Plant Biol. 8:116.
12) Cromwell O, Hafner D, Nandy A. (2011). "Recombinant allergens for specific immunotherapy" J Allergy Clin Immunol. 127(4):865-872
13) Ma Y, Gadermayer G, Bohle B, Bolhaar S, Knulst A, Markovic-Housley Z, Breiteneder H, Briza P, Hoffmann-Sommergruber K, Ferreira F. (2006). "Mutational analysis of amino acid positions crucial for IgE-binding epitope of the major apple (*Malus domestica*) allergen, Mal d 1". Int Arch Allergy Immunol 139:53-62.
14) Neudecker P, Lehmann K, Nerkamp J, Haase T, Wangorsch A, Fotish K, Hoffmann S, Rosch P, Vieths S, Scheurer S. (2003) "Mutational epitope analysis of Pru av 1 and Api g 1, the major allergens of cherry (*Prunus avium*) and celery (*Apium graveolens*): correlating IgE reactivity with three-dimensional structure". Biochem J. 376:97-107.

15) Wiche R, Gubesch M, Konig H, Fötisch K, Hoffmann A, Wangorsch A, Scheurer S, Vieths S. (2005) "Molecular basis of pollen-related food allergy: identification of a second cross-reactive IgE epitope on Prua v 1, the major (*Prunus avium*) allergen". Biochem J. 385:319-327.

16) Gajhede M, Osmark P, Poulsen F M, Ipsen H, Larsen J N, Joost van Neerven R J, Schou C, Lowenstein H, and Spangfort M D. (1996). "X-ray and NMR structure of Bet v 1, the origin of birch pollen allergy". Nat. Struct. Biol. 3:1040-1045.

17) Holm J, Gajhede M, Ferreras M, Henriksen A, Ipsen H, Larsen J N, Lund L, Jacobi H, Millner A, Wurtzen P A, Spangfort M D. (2004). "Allergy vaccine engineering: epitope modulation of recombinant Bet v 1 reduces IgE binding but retains protein folding pattern for induction of protective blocking-antibody responses". The journal of Immunology. 173:5258-5267.

18) Klingmayr E, Hauser M, Zimmermann F, Dissertori O, Lackner P, Wopfner N, Ferreira F, Wallner M. (2009). "Identification of B-cell epitope of Bet v 1 involved in cross-reactivity with food allergens" Allergy; 64:647-651

19) Purohit A, Niederberger V, Kronqvist M, Horak F, Gronneberg R, Suck R, Weber B, Fiebig H, van Hage M, Pauli G, Valenta R, Cromwell O. (2008). "Clinical effects of immunotherapy with genetically modified recombinant birch pollen Bet v 1 derivatives". Clin Exp Allergy. 38(9):1514-25.

20) Reese G, Ballmer-Weber B, Wangorsch A, Randow S, Vieths S. (2007) "Allergenicity and antigenicity of wild-type and mutant, monomeric, and dimeric carrot major allergen Dau c 1: destruction of conformation, not oligomerization, is the roadmap to save allergen vaccines". J allergy Clin Immunology 119:944-951.

21) Wang W., Malcolm B A. (2002). "Two-stage polymerase chain reaction protocol allowing introduction of multiple mutations, deletions, and insertions, using QuikChange site-directed mutagenesis". Methods Mol. Biol.; 182: 37-43.

22) Cryz, S. J. (1991), "Immunotherapy and Vaccines", VCH Verlagsgesellschaft.

23) Asturias J A, Ibarrola I, Eseverri J L, Arilla M C, Gonzales-Rioja R, Martinez A. (2004). "PCR-based cloning and immunological characterization of *Parietaria judaica* pollen profilin". J Investig Allergol Clin Immunol, 14: 43-48.

24) Holm J, Ferreras M, Ipsen H, Wurtzen P A, Gajhede M, Larsen J N, Lund L, Spangfort M D. (2011). "Epitope grafting, re-creating a conformational Bet v 1 antibody epitope on the surface of the homologous apple allergen Mal d 1". J Biol. Chem. 286:17569-78.

The invention claimed is:

1. A sequence variant of the *Malus domestica* major allergen, Mal d 1, said sequence variant showing reduced IgE reactivity relative to a wild-type Mal d 1 allergen, wherein said sequence variant is characterized by two alanine substitutions at positions 25 and 78 and otherwise having the sequence set forth in SEQ ID NO:1.

* * * * *